US 9,101,679 B2

(12) United States Patent
Robitaille et al.

(10) Patent No.: US 9,101,679 B2
(45) Date of Patent: Aug. 11, 2015

(54) STERILIZATION METHOD AND APPARATUS

(75) Inventors: Simon Robitaille, Charny (CA); Sylvie Dufresne, Quebec (CA); Jean-Martin Vallieres, Quebec (CA); Cynthia Martel, Quebec (CA); Helene Leblond, Quebec (CA); Nancy Dassie, Lac Beauport (CA); Marie-Christine Gagne, Ste-Brigitte-de-Laval (CA); Karine Martel, St-Augustine-de-Desmaures (CA); Claudia Bedard, Quebec (CA); Bruno Tremblay, Quebec (CA)

(73) Assignee: TS03 Inc., Quebec (CA)

( * ) Notice: Subject to any disclaimer, the term of this patent is extended or adjusted under 35 U.S.C. 154(b) by 0 days.

(21) Appl. No.: 12/893,742

(22) Filed: Sep. 29, 2010

(65) Prior Publication Data

US 2011/0076192 A1 Mar. 31, 2011

Related U.S. Application Data

(60) Provisional application No. 61/247,197, filed on Sep. 30, 2009.

(51) Int. Cl.
*A61L 2/20* (2006.01)
*B65D 23/00* (2006.01)

(52) U.S. Cl.
CPC . *A61L 2/208* (2013.01); *A61L 2/20* (2013.01); *A61L 2/202* (2013.01); *B65D 23/001* (2013.01);
(Continued)

(58) Field of Classification Search
CPC .............. A61L 2/16; A61L 2/20; A61L 2/202; A61L 2/208; A61L 2202/122; A61L 2202/14; A61L 2202/15; A61L 2202/24
USPC ........................ 422/28, 29, 33, 292
See application file for complete search history.

(56) References Cited

U.S. PATENT DOCUMENTS 3,717,274 A 2/1973 Wingardh
(Continued)

FOREIGN PATENT DOCUMENTS

EP 0298694 1/1989
(Continued)

OTHER PUBLICATIONS

Favero, "Disinfection and sterilization in healthcare facilities", Chapter 2, Biocides Development, Ed. Zhu ACS Symposium Series, American Chemical Society, Washington, DC, Sep. 7, 2007, pp. 31-50.
(Continued)

*Primary Examiner* — Timothy Cleveland
(74) *Attorney, Agent, or Firm* — Borden Ladner Gervais LLP

(57) ABSTRACT

A method of sterilizing an article by sequentially exposing the article to hydrogen peroxide and ozone is disclosed. The article is exposed under vacuum first to an evaporated aqueous solution of hydrogen peroxide and subsequently to an ozone containing gas. The exposure is carried out without reducing the water vapor content of the sterilization atmosphere, the water vapor content being derived from the aqueous solvent of the hydrogen peroxide solution and from the decomposition of the hydrogen peroxide into water and oxygen. The complete sterilization process is carried out while the chamber remains sealed and without removal of any component of the sterilization atmosphere. For this purpose, the chamber is initially evacuated to a first vacuum pressure sufficient to cause evaporation of the aqueous hydrogen peroxide at the temperature of the chamber atmosphere. The chamber is then sealed for the remainder of the sterilization process and during all sterilant injection cycles. Keeping the chamber sealed and maintaining the hydrogen peroxide and its decomposition products in the chamber for the subsequent ozone sterilization step results in a synergistic increase in the sterilization efficiency and allows for the use of much lower sterilant amounts and sterilization cycle times than would be expected from using hydrogen peroxide and ozone in combination.

10 Claims, 12 Drawing Sheets

(52) U.S. Cl.
CPC ........ *A61L 2202/122* (2013.01); *A61L 2202/13* (2013.01); *A61L 2202/14* (2013.01); *A61L 2202/24* (2013.01)

(56) References Cited

U.S. PATENT DOCUMENTS

| | | | |
|---|---|---|---|
| 3,880,011 A | 4/1975 | Johnson | |
| 3,978,232 A | 8/1976 | Dodsworth et al. | |
| 4,434,820 A | 3/1984 | Glass | |
| 4,458,348 A | 7/1984 | Fukuda et al. | |
| 4,548,348 A | 10/1985 | Clements | |
| 4,642,165 A | 2/1987 | Bier | |
| 4,838,887 A | 6/1989 | Idriss | |
| 4,952,370 A | 8/1990 | Cummings et al. | |
| 4,956,145 A | 9/1990 | Cummings et al. | |
| 5,445,792 A | 8/1995 | Rickloff | |
| 5,508,009 A * | 4/1996 | Rickloff et al. | 422/292 |
| 5,556,607 A | 9/1996 | Childers et al. | |
| 5,700,426 A | 12/1997 | Schmitthaeusler et al. | |
| 6,070,761 A | 6/2000 | Bloom et al. | |
| 6,096,266 A | 8/2000 | Duroselle | |
| 6,488,650 B1 | 12/2002 | Epstein et al. | |
| 7,048,887 B2 | 5/2006 | Frost et al. | |
| 7,186,371 B1 * | 3/2007 | Watling | 422/33 |
| 2003/0066346 A1 | 4/2003 | Goloby | |
| 2004/0022673 A1 | 2/2004 | Protic | |
| 2004/0146427 A1 | 7/2004 | Awakowicz et al. | |
| 2007/0020141 A1 | 1/2007 | Chiffon et al. | |
| 2007/0098591 A1 | 5/2007 | Frinke et al. | |
| 2007/0258855 A1 * | 11/2007 | Turcot et al. | 422/33 |
| 2008/0233002 A1 | 9/2008 | Mizuno et al. | |

FOREIGN PATENT DOCUMENTS

| | | |
|---|---|---|
| EP | 1121942 | 8/2001 |
| EP | 1177986 | 2/2002 |
| EP | 1736175 A1 | 12/2006 |
| FR | 2852849 | 10/2004 |
| JP | 54-163993 | 11/1979 |
| JP | 04-054698 | 5/1992 |
| JP | 08-505787 | 6/1996 |
| JP | 3182658 | 7/2001 |
| JP | 2001-289687 | 10/2001 |
| JP | 2002-206655 | 7/2002 |
| JP | 2002-360672 | 12/2002 |
| JP | 2006-036343 | 2/2006 |
| JP | 2006-305379 | 11/2006 |
| JP | 2007-521118 | 8/2007 |
| JP | 2008-178479 | 8/2008 |
| JP | 2008-200511 | 9/2008 |
| WO | 89/06140 | 7/1989 |
| WO | 93/17726 | 9/1993 |
| WO | 00/02595 A1 | 1/2000 |
| WO | 2005094907 A1 | 10/2005 |
| WO | 2009/008755 | 1/2009 |
| WO | 2009005252 A2 | 1/2009 |

OTHER PUBLICATIONS

McDonnell, "Peroxygens and other forms of oxygen: their use for effective cleaning, disinfection, and sterilization", Chapter 13, New Biocides Development, Ed. Zhu, ACS Symposium Series, American Chemical Society, Washington, DC., Sep. 7, 2007, pp. 292-308.
Kulla et al., "Sterilizing combination products using oxides of nitrogen", Medical Device and Diagnostic Industry, Mar. 2009, 6 pages.
International Patent Application No. PCT/CA2010/001518, International Search Report dated Jan. 13, 2011.
Extended European Search Report dated May 31, 2013, European Patent Application No. 13158399.9.
Extended European Search Report dated May 2, 2013, European Patent Application No. 13158378.3.
Extended European Search Report dated May 7, 2013, European Patent Application No. 13158381.7.
Extended European Search Report dated May 7, 2013, European Patent Application No. 13158395.7.
Extended European Search Report dated May 7, 2013, European Patent Application No. 13158388.2.
Extended European Search Report dated May 7, 2013, European Patent Application No. 13158404.7.
Extended European Search Report dated May 31, 2013, European Patent Application No. 10819766.6.
Patent Examination Report dated Apr. 5, 2013, Australian Patent Application No. 2013201176.
Patent Examination Report dated Jun. 18, 2013, Australian Patent Application No. 2013201199.
English Translation of Japanese Patent Application No. 2012-531191, Office Action dated Jul. 2, 2013.
European Patent Application No. 13158399.9, Office Action dated Mar. 4, 2014.
European Patent Application No. 13158381.7, Office Action dated Feb. 11, 2014.
European Patent Application No. 13158404.7, Office Action dated Feb. 11, 2014.
European Patent Application No. 13158395.7, Office Action dated Feb. 11, 2014.
English Translation of Japanese Patent Application No. 2013-083152 Office Action dated Oct. 21, 2014.
English Translation of Japanese Patent Application No. 2013-083238 Office Action dated Oct. 21, 2014.
English Translation of Japanese Patent Application No. 2013-083142 Office Action dated Sep. 30, 2014.
English Translation of Japanese Patent Application No. 2013-083154 Office Action dated Oct. 21, 2014.
English Translation of Japanese Patent Application No. 2013-083229 Office Action dated Oct. 21, 2014.
English Translation of Japanese Patent Application No. 2013-083146 Office Action dated Oct. 21, 2014.
European Patent Application No. 13158395.7-1356 Office Action dated Nov. 19, 2014.

* cited by examiner

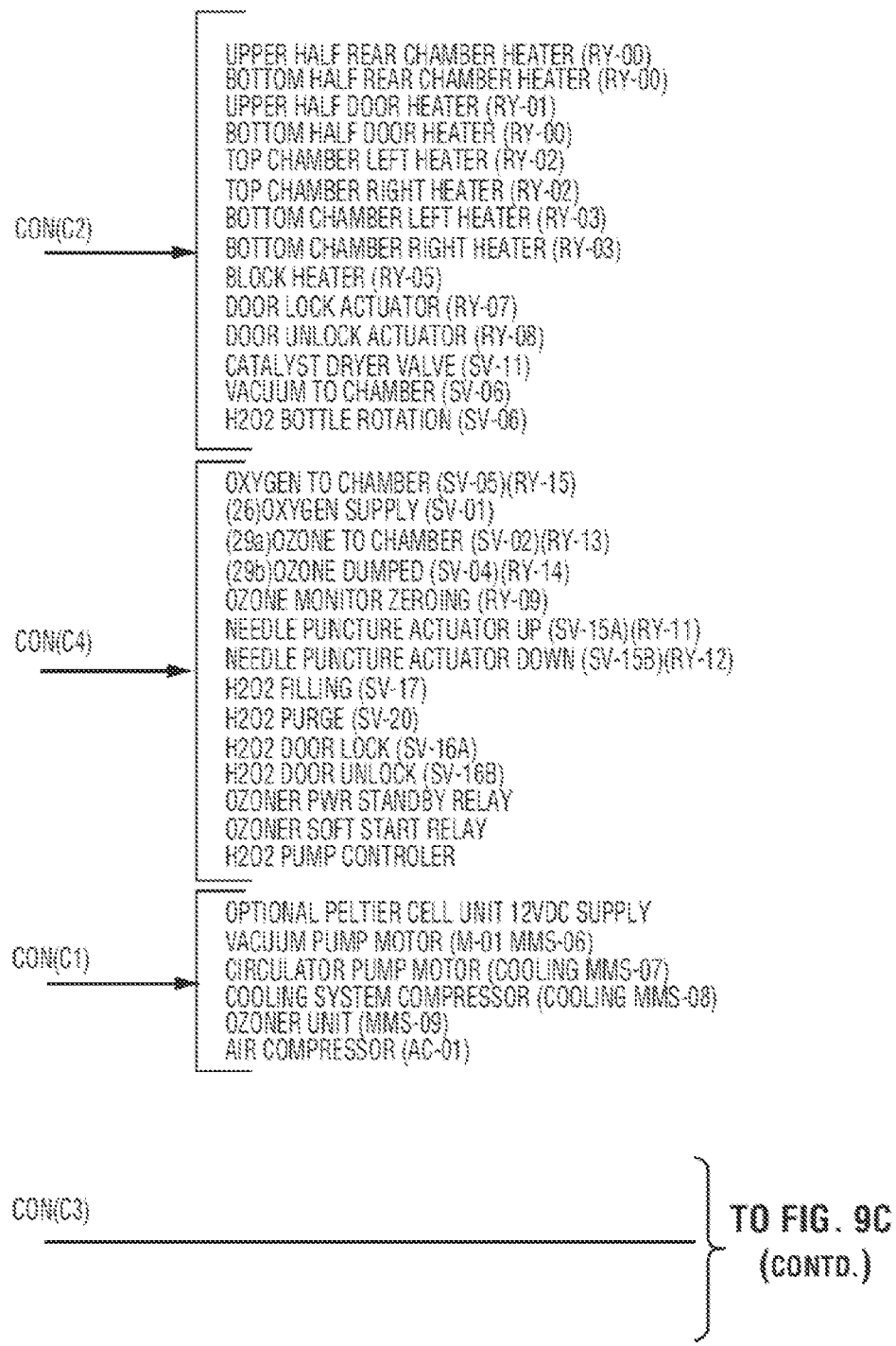
FIG. 9B (CONTD.)

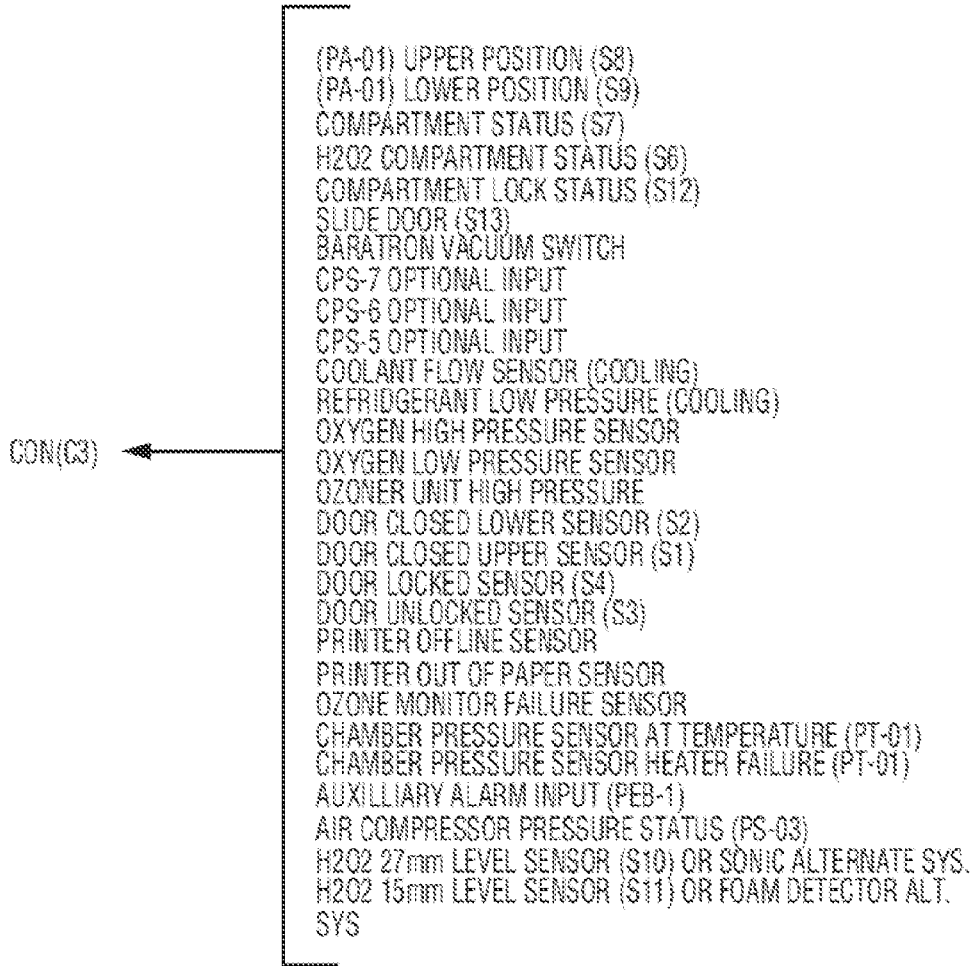
FIG. 9C (CONTD.)

STERILIZATION METHOD AND APPARATUS

CROSS-REFERENCE TO RELATED APPLICATIONS

This application claims priority from U.S. Provisional Application U.S. Ser. No. 61/247,197, filed Sep. 30, 2009 and entitled Sterilization Method And Apparatus, which is incorporated herein by reference in its entirety.

FIELD OF THE INVENTION

The present invention relates generally to sterilization methods and apparatus. More particularly, the present invention relates to a sterilization process using gaseous biocides under vacuum

BACKGROUND OF THE INVENTION

Sterilization is the destruction of any virus, bacteria, fungus or other micro-organism, whether in a vegetative or in a dormant spore state and is defined by a $10^{-6}$ reduction in the level of bacteria. Conventional sterile processing procedures for medical instruments involve high temperature (such as steam and dry heat units) or chemicals (such as ethylene oxide gas, hydrogen peroxide, or ozone).

Sterilization methods and apparatus using gaseous sterilants are well known. Sterilizers using hydrogen peroxide as the sterilant are widely used. The hydrogen peroxide is generally supplied as an aqueous solution and evaporated prior to injection into a sterilization chamber of the sterilizer, by heating of the solution, or by applying a vacuum to the sterilization chamber, or both. After evaporation of the solution, the sterilization atmosphere in the sterilization chamber includes water vapor and hydrogen peroxide gas. It is a disadvantage of this process that the water vapor tends to condensate on articles in the chamber as the sterilization proceeds. The resulting layer of water condensate on the articles to be sterilized interferes with the sterilizing action of the hydrogen peroxide. Numerous apparatus and process modifications have been developed to address this problem, all of which are aimed at limiting the relative humidity in the sterilization atmosphere during the sterilization process. However, these modifications invariably increase operating cost and/or sterilization cycle times.

Sterilizers using ozone containing gas as the sterilant are also known. The ozone gas is generally produced externally to the sterilization chamber and supplied into the chamber under vacuum to increase penetration of the sterilant gas into restricted spaces on the articles to be sterilized. In order to improve the sterilization effect of ozone gas, the sterilization atmosphere is generally humidified with water prior to the injection of ozone gas into the sterilization chamber. However, the amount of ozone gas needed is relatively high (85 mg/l) and the sterilization cycle times are relatively long, making ozone based sterilization processes comparatively expensive. Furthermore, many articles to be sterilized are damaged by the high levels of ozone required to achieve complete sterilization and can therefore not be sterilized in an ozone sterilization process.

Sterilization processes using both hydrogen peroxide gas and ozone gas have been used, but with unsatisfactory results especially with respect to the sterilization of articles with long internal lumens, such as gastroscopes and colonoscopes, and with respect to cycle times and sterilization cost. Although ozone based processes are satisfactory with respect to sterilization of articles with long lumens, material compatibility represents a problem. Hydrogen peroxide based processes are generally unsatisfactory regarding the sterilization of long lumens.

Therefore, a method and apparatus is desired which would address at least one of the disadvantages of known sterilization processes using gaseous sterilants.

SUMMARY OF THE INVENTION

It is an object of the present invention to obviate or mitigate at least one disadvantage of previous sterilization processes using gaseous sterilants.

In a first aspect, the invention provides a method for sterilizing an article by sequentially exposing an article to be sterilized under vacuum to a conditioning agent and to an ozone containing gas. The conditioning agent initiates the formation of free radicals and accelerates the formation of hydroxyl radicals from ozone.

The conditioning agent is preferably hydrogen peroxide, acidic water, carbonated water, peracetic acid, acetic acid, alcohol, ethanol or methanol. The sterilant gas is preferably ozone, nitrogen oxide or chlorine dioxide, preferably ozone.

In an embodiment of the first aspect, there is provided a method for sterilizing an article by sequentially exposing an article to be sterilized first to the conditioning agent for forming free radicals, such as hydrogen peroxide, and then to a sterilizing gas which is a chemical for creating or regenerating the free radicals, such as ozone ($O_3$), nitrogen oxide (NO) or Chlorine dioxide ($ClO_2$). The article is preferably exposed under vacuum first to an evaporated aqueous solution of hydrogen peroxide and subsequently to the sterilant gas. The preferred combination of conditioning agent and sterilant gas is hydrogen peroxide with ozone.

In a second aspect, the invention provides a method for sterilizing an article by sequentially exposing an article to be sterilized under vacuum to an evaporated aqueous solution of hydrogen peroxide and to an ozone containing gas without reducing the humidity of the sterilization atmosphere during the sterilization with either sterilant.

In an embodiment of the second aspect, there is provided a method for sterilizing an article by sequentially exposing an article to be sterilized first to hydrogen peroxide and then to ozone. The article is preferably exposed under vacuum first to an evaporated aqueous solution of hydrogen peroxide and subsequently to an ozone containing gas. Preferably, the exposure is carried out without reducing the water vapor content of the sterilization atmosphere, the water vapor content being derived from the aqueous solvent of the hydrogen peroxide solution and from the decomposition of the hydrogen peroxide into water and oxygen.

Most preferably, evaporated hydrogen peroxide and ozone containing gas are sequentially added to the chamber and maintained in the chamber for a preselected exposure time. All removal of any components in the sterilization atmosphere is stopped during addition of the sterilants and for the duration of the exposure time and the chamber remains sealed. For this purpose, the chamber is initially evacuated to a first vacuum pressure sufficient to cause evaporation of the aqueous hydrogen peroxide at the temperature of the chamber atmosphere. The chamber is then sealed for the remainder of the sterilization process, which simplifies the process and, as will be discussed below, leads to a surprising increase in sterilization efficacy.

In a further aspect, there is provided a method for sterilizing an article in a sealable sterilization chamber, comprising the steps of placing the article into the sterilization chamber, sealing the chamber; applying to the chamber a vacuum of a first pressure sufficient to evaporate an aqueous solution of hydrogen peroxide at the temperature of an atmosphere in the chamber; evaporating an aqueous hydrogen peroxide solution into the sealed chamber; terminating the evaporating once a preselected second pressure, higher than the first pressure, is reached in the sealed sterilization chamber; maintaining the chamber sealed for a first exposure period during which hydrogen peroxide gas in the chamber decomposes into free radicals, injecting, after the first exposure period, into the chamber a dry ozone containing gas and without humidification of the ozone containing gas or the chamber atmosphere and until a third pressure, higher than the second pressure, is reached in the chamber, maintaining the chamber sealed for a second exposure period, interrupting all removal of any component of the sterilization atmosphere after applying the vacuum and prior to the evaporating step, until an end of the second exposure period; removing residual sterilants from the chamber, and taking the sterilized article from the chamber. The second exposure period can be omitted and the dry ozone containing gas injected right after the preselected second pressure is reached.

The steps between and including the applying and removing steps are preferably repeated at least once. The first pressure is preferably 1 Torr, the second pressure is preferably 20 Torr and the amount of dry ozone injected per volume of the sterilization atmosphere is preferably 1-10 mg/l.

In another aspect, the invention provides a hydrogen peroxide delivery system for a sterilizer having a hydrogen peroxide injection unit and a housing, comprising a stand for supporting a hydrogen peroxide solution container in an upright position within the housing, a drainage arrangement connected with the stand for aspirating the hydrogen peroxide solution from the container, and a delivery arrangement connected with the drainage arrangement for supplying the aspirated hydrogen peroxide solution to the hydrogen peroxide injection unit, the drainage arrangement including a drainage needle connected with the delivery arrangement for penetrating a seal on the container and extending into the hydrogen peroxide solution in the container, and a reciprocatable needle drive for moving the needle from an at rest position, wherein the needle is retracted to allow insertion of a new hydrogen peroxide container into the stand, to a penetrating position wherein the needle penetrates the seal of the container and extends into the hydrogen peroxide solution in the container, the needle extending all the way to a bottom of the container in the penetrating position.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 10b is a cross-sectional view of the container of FIG. 10a;

FIG. 10c is a side elevational view of the container of FIG. 10a; and

DETAILED DESCRIPTION OF THE PREFERRED EMBODIMENT

Figure 1:
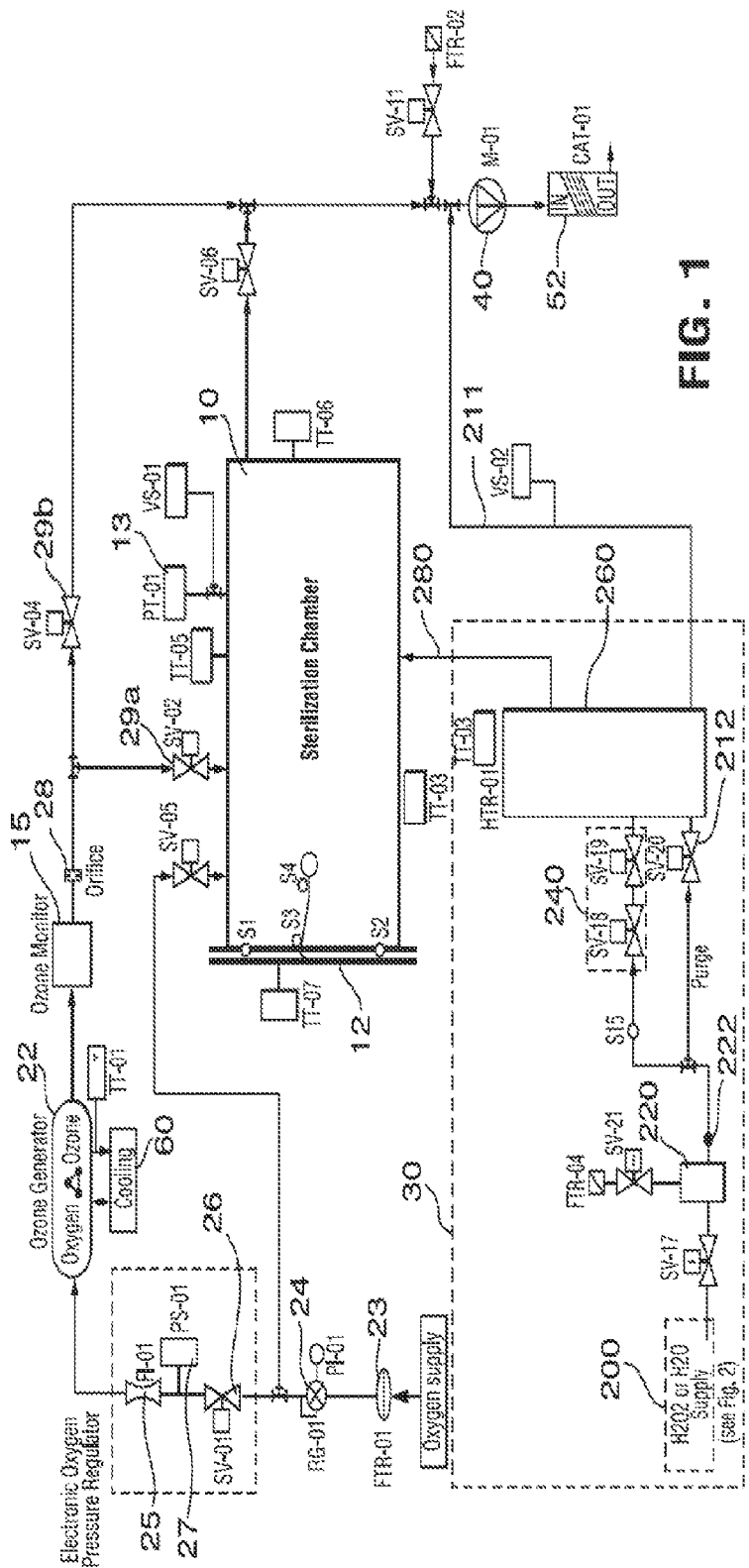
FIG. 1 shows a schematic diagram of an apparatus in accordance with the invention, the illustrated parts of the apparatus being listed in Table III.

Generally, the present invention provides a method and system for sterilization of an article in a gaseous sterilization atmosphere by sequentially adding evaporated hydrogen peroxide and ozone.

In a first aspect, the invention provides a method for sterilizing an article in a sealable sterilization chamber, comprising the steps of
 a. placing the article into the sterilization chamber,
 b. sealing the chamber,
 c. applying to the chamber a vacuum of a first pressure,
 d. injecting into the sealed chamber a gaseous conditioning agent for forming free radicals,
 e. maintaining the chamber sealed for a first exposure period,
 f. injecting, after the first exposure period, a sterilant gas for creating or regenerating the free radicals into the sealed chamber,
 g. maintaining the chamber sealed for a second exposure period,
 h. removing residual sterilant from the chamber at the end of the second exposure period, and
 i. removing the sterilized article from the chamber.

The conditioning agent is preferably hydrogen peroxide, acidic water, carbonated water, peracetic acid, acetic acid, alcohol, ethanol or methanol and the sterilant gas is preferably ozone, nitrogen oxide or chlorine dioxide. Most preferably, the conditioning agent is hydrogen peroxide and the sterilant gas is ozone.

In a second aspect, the invention provides a method for sterilizing an article in a sealable sterilization chamber, comprising the steps of
 j. placing the article into the sterilization chamber,
 k. sealing the chamber,
 l. applying to the chamber a vacuum of a first pressure sufficient to evaporate an aqueous solution of hydrogen peroxide at the temperature of an atmosphere in the chamber,
 m. evaporating an aqueous hydrogen peroxide solution into the sealed chamber,
 n. terminating the evaporating once a preselected second pressure, higher than the first pressure, is reached in the sealed sterilization chamber,
 o. injecting a dry ozone or nitric oxide containing gas into the chamber, p. maintaining the chamber sealed for a second exposure period, q. interrupting all removal of any component of the sterilization atmosphere after applying the vacuum and prior to the evaporating step, until an end of the second exposure period;

r. removing residual sterilant from the chamber at the end of the second exposure period, and s. removing the sterilized article from the chamber.

In a preferred embodiment, the method includes the further step f) of maintaining the chamber sealed for a first exposure period during which hydrogen peroxide gas in the chamber decomposes into free radicals, wherein the dry ozone or nitric oxide containing gas is injected after the first exposure period.

Preferably, the step d) of evaporating the hydrogen peroxide solution includes injecting repeated pulses of hydrogen peroxide solution at a pulse volume of less than 75 μL, preferably less than 35 μL, most preferably at a pulse volume of about 20 μL. Steps c) to j) are preferably repeated at least once. The preferred solution is 50% hydrogen peroxide solution. The first pressure is preferably 1 Torr (1.33 mbar). The second pressure is preferably 17-54 Torr, more preferably 20 Torr. Preferably, an amount ozone in the range of 1-10 mg per liter of sterilization atmosphere is injected in the injecting step.

In a third aspect, the invention provides a hydrogen peroxide delivery system for a sterilizer having a hydrogen peroxide injection unit and a housing, comprising a cradle for supporting a hydrogen peroxide solution container in an upright position within the housing, a drainage arrangement connected with the cradle for aspirating the hydrogen peroxide solution from the container, and a delivery arrangement connected with the drainage arrangement for supplying the aspirated hydrogen peroxide solution to the hydrogen peroxide injection unit, the drainage arrangement including a drainage needle connected with the delivery arrangement for penetrating a seal on the container and extending into the hydrogen peroxide solution in the container, and a reciprocatable needle drive for moving the needle from an at rest position, wherein the needle is retracted to allow insertion of a new hydrogen peroxide container into the cradle, to a penetrating position wherein the needle penetrates the seal of the container and extends into the hydrogen peroxide solution in the container, the needle extending all the way to a bottom of the container in the penetrating position.

The drainage arrangement preferably includes a force sensor for detecting engagement of the needle with the container bottom and terminating needle advance to avoid penetration of the container bottom by the needle. The force sensor is preferably incorporated in the needle drive. Preferably, the delivery system further includes an ultrasonic sensor for detecting when the hydrogen peroxide liquid in the container drops below a predetermined level. The sensor is preferably spring biased against the container, when the container is supported on the stand.

In a fourth aspect, the invention provides a hydrogen peroxide solution container, comprising a hollow body with a top end including a fill and drainage opening, a side wall and a conical bottom, a stand for maintaining the container in an upright position on a flat horizontal surface and a connecting arrangement for connecting the stand to the body, the arrangement including an external recess in the side wall of the body and the stand being cup-shaped and having a radially inwardly extending tab for engagement with the recess to provide a snap fit connection of the stand to the body. The recess is preferably a circumferentially extending, continuous groove and the stand preferably includes at least two tabs for engagement of the groove. More preferably, the recess is a circumferentially extending, continuous groove and the tab is a circumferentially extending flange at a top end of the stand for snap fit engagement with the recess. Alternatively, the body includes at least two recesses and the stand includes a corresponding number of tabs positioned on the stand for snap fit engagement with one of the recesses respectively.

In a fifth aspect, the invention provides a hydrogen peroxide metering unit for a hydrogen peroxide sterilizer, comprising body defining a metering passage having a fixed volume and upstream and downstream ends, an upstream connection for connecting the upstream end to a hydrogen peroxide supply, a downstream connection for connecting the downstream end to a hydrogen peroxide vaporizer, an upstream valve for selectively closing the upstream end and a downstream valve for selectively closing the downstream end, and a controller for operating the valves in a non-overlapping and opposite manner for selectively preventing opening of both valves at the same time.

The controller preferably sequentially operates the valves for sequential connection of the metering passage to the hydrogen peroxide supply and the vaporizer. Preferably, the volume of the passage is known, the evaporator is under vacuum and the controller tracks the number of valve operating cycles for determination of an injected volume of hydrogen peroxide from the number of cycles and the volume of the metering passage.

In a sixth aspect, the invention provides a method of controlling unwanted condensation of hydrogen peroxide in a sterilization chamber at a preselected temperature, comprising maintaining the sterilization chamber at a vacuum pressure below the pressure at which hydrogen peroxide will boil at the preselected temperature, evaporating successive pulses of hydrogen peroxide, and injecting the evaporated hydrogen peroxide into the chamber, whereby the volume of each pulse of hydrogen peroxide is less than 75 μL, preferably less than 35 μL, most preferably less than 20 μL.

In a seventh aspect, the invention provides a method of metering a preselected volume of hydrogen peroxide into an evaporator under vacuum, comprising the steps of a) connecting a passage of known volume to the evaporator under vacuum to evacuate the passage;

b) sealing the passage;

c) connecting the passage to a supply of hydrogen peroxide solution for a time sufficient to draw the hydrogen peroxide solution into the evacuated passage and fill the passage with the hydrogen peroxide solution;

d) sealing the passage; and e) repeating steps a) to d) X number of times, X being the ratio of preselected volume/known volume.

In an eighth aspect, the invention provides a method of metering hydrogen peroxide gas into an evacuated sterilization chamber, comprising the steps of a) continuously monitoring a pressure in the sterilization chamber;

b) connecting a passage of known volume to the evacuated sterilization chamber for evacuating the passage;

c) sealing the passage;

d) connecting the evacuated passage to a supply of hydrogen peroxide solution for a time sufficient to draw the hydrogen peroxide solution into and fill the passage with the hydrogen peroxide solution;

e) sealing the passage; and f) repeating steps a) to d) until a preselected pressure increase in the sterilization chamber is detected.

The pressure increase is preferably 19 Torr.

In a ninth aspect, the invention provides a method of metering hydrogen peroxide gas into an evacuated sterilization chamber, comprising the steps of
  a) continuously monitoring a pressure in the sterilization chamber;
  b) connecting a metering passage of known volume to the evacuated sterilization chamber for evacuating the metering passage;
  c) sealing the metering passage;
  d) connecting the evacuated metering passage to a supply of hydrogen peroxide solution for a time sufficient to draw the hydrogen peroxide solution into and fill the metering passage with the hydrogen peroxide solution;
  e) sealing the metering passage; and
  f) repeating steps a) to d),
whereby the known volume of the metering passage is between 75 µL and 15 µL, preferably between 35 µL and 15 µL, more preferably 20 µL and 15 µL.

Figure 3:
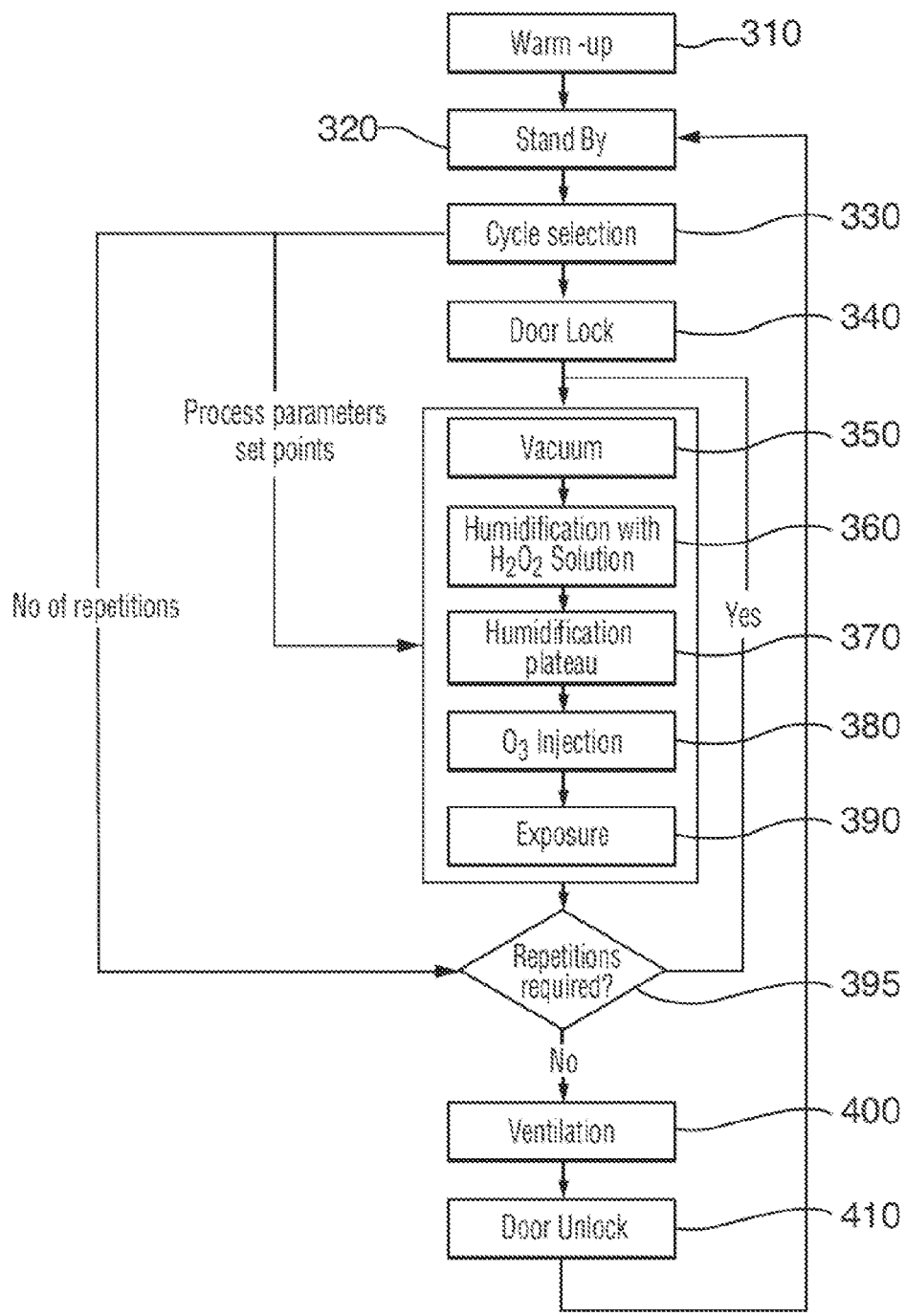
FIG. 3 is a flow diagram of a preferred sterilization method in accordance with the invention.
Figure 4:
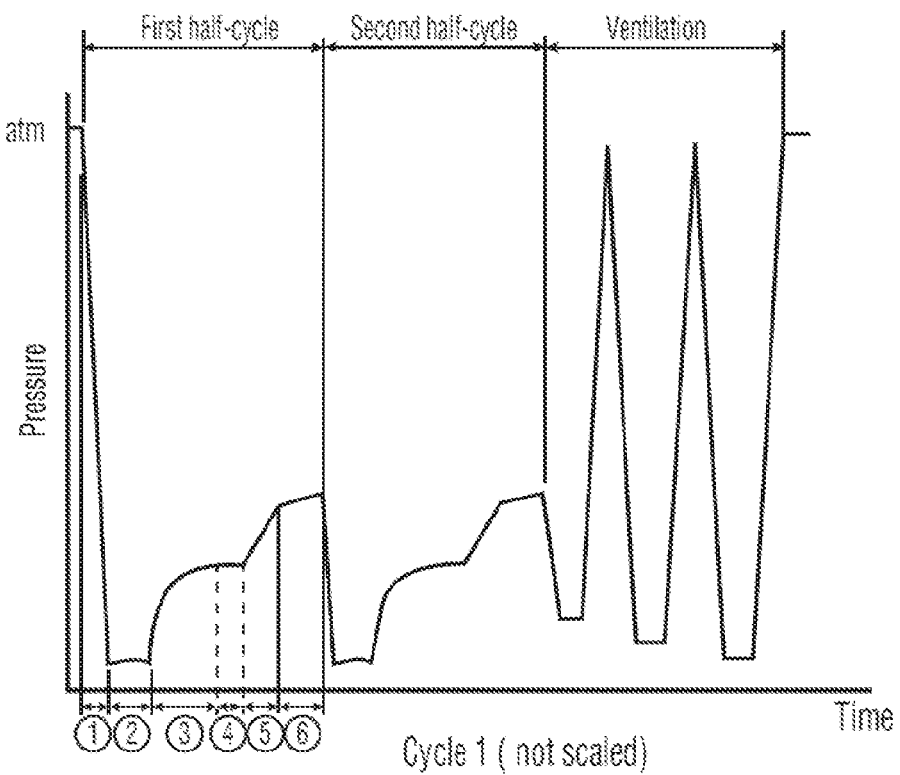
FIG. 4 is a graph illustrating a first exemplary sterilization cycle in accordance with the invention.
Figure 5:
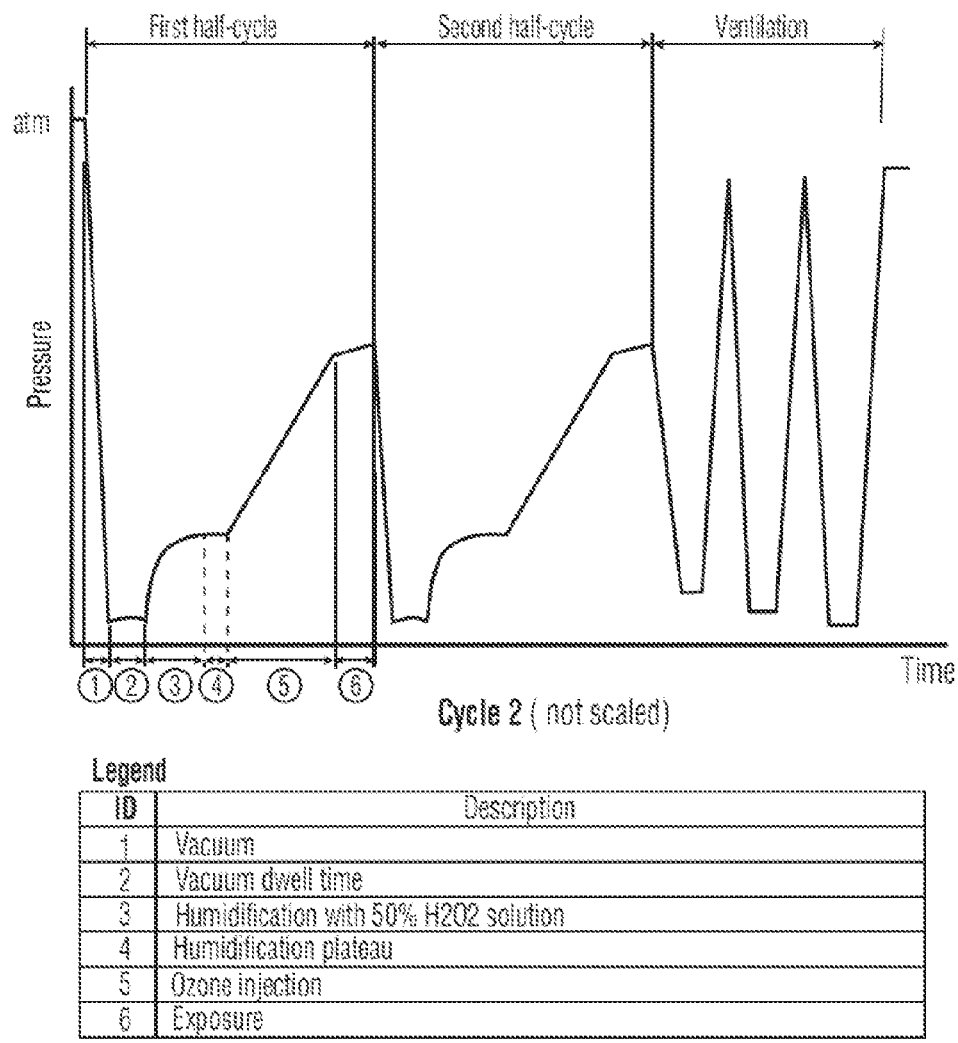
FIG. 5 is a graph illustrating a second exemplary sterilization cycle in accordance with the invention.
Figure 6:
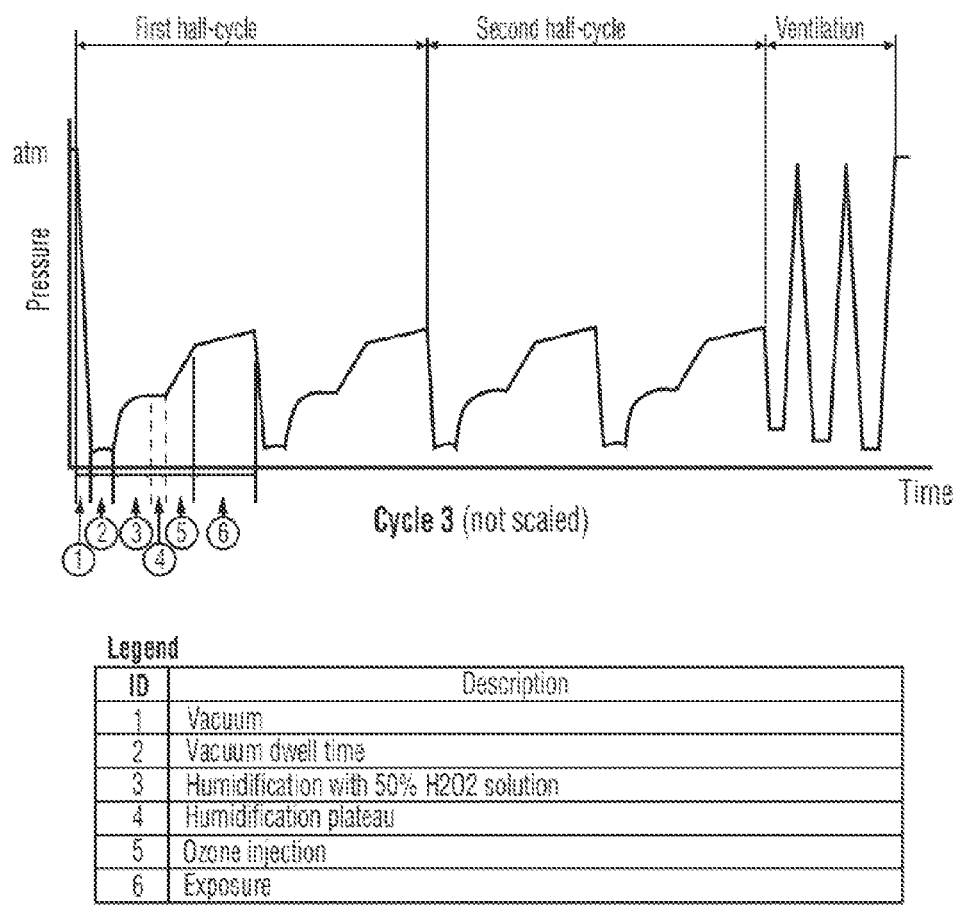
FIG. 6 is a graph illustrating a third exemplary sterilization cycle in accordance with the invention.

In one embodiment, as illustrated in the flow diagram of FIG. 3 and the cycle graphs of FIGS. 4 to 6, the invention provides a method of sterilizing an article by exposing an article to be sterilized sequentially to hydrogen peroxide and ozone. The article is preferably exposed under vacuum first to an evaporated aqueous solution of hydrogen peroxide and subsequently to an ozone containing gas. Preferably, the exposure is carried out without reducing the water vapor content of the sterilization atmosphere, the water vapor content being derived from the aqueous solvent of the hydrogen peroxide solution and from the decomposition of the hydrogen peroxide into water and oxygen. Most preferably, the complete sterilization process is achieved while the chamber remains sealed and without removal of any component of the sterilization atmosphere. For this purpose, the chamber is initially evacuated to a first vacuum pressure sufficient to cause evaporation of the aqueous hydrogen peroxide at the temperature of the chamber atmosphere. The chamber is then sealed and hydrogen peroxide and ozone containing gas are sequentially added to the chamber and maintained in the chamber for a preselected exposure time. All removal of any components in the sterilization atmosphere is stopped during addition of the sterilants and for the duration of the exposure time.

The aqueous hydrogen peroxide solution is evaporated and directly injected into the sterilization chamber without any measures to reduce the water vapor content. The inventors of the present application have surprisingly discovered that the amount of sterilants used and the length of the sterilization cycle can be significantly reduced, when any and all steps to reduce the water vapor content in the chamber are omitted and the hydrogen peroxide sterilization step is followed by an ozone sterilization step, since the water vapor generated during the hydrogen peroxide sterilization step can be used to sufficiently humidify the atmosphere in the chamber to improve the ozone sterilization step. Much lower amounts of hydrogen peroxide and ozone can be used than in prior art processes using the same sterilants, while still achieving complete sterilization. Also, the required amounts of the sterilants in accordance with the present invention are lower than what would be expected from simply using the two sterilants in the same cycle. Thus, maintaining the chamber sealed throughout all sterilization steps without any measures to control the humidity in the sterilization atmosphere appears to result in a synergistic effect.

A sterilizer in accordance with the invention as illustrated schematically in FIG. 1 operates generally in the following manner. An article to be sterilized (not shown) is placed into a sterilization chamber 10 and the chamber is sealed. A vacuum is applied to the chamber 10. Evaporated hydrogen peroxide solution is supplied into the sterilization chamber 10 from a delivery unit 30 (see FIG. 8), which will be discussed in more detail below. The evaporated hydrogen peroxide supplied into the chamber provides a partial sterilization of the article. Medical quality oxygen is subjected in an ozone generator 22 to an electrical field, which converts the oxygen into ozone containing gas. The ozone containing gas is then fed into the chamber 10, which has been humidified by the injection of the evaporated hydrogen peroxide solution and the decomposition of the hydrogen peroxide into free radicals (hydroxyls), water and oxygen. The ozone containing gas finishes the sterilization of the article. Remaining sterilant gases are subsequently decomposed into water and oxygen using a catalyst 52. The only residues left at the end of the sterilization cycle are oxygen and clean water.

The ozone sterilization method of the invention is preferably carried out at room temperature and, thus, requires substantially no aeration or cooling down of sterilized articles so that they can be used immediately following the sterilization cycle. Moreover, the gases used diffuse more quickly into long lumens to be sterilized, reducing the cycle times required for sterilization. This allows hospitals to reduce the cost of maintaining expensive medical device inventories. The sterilization method of the invention offers several further advantages. It produces no toxic waste, does not require the handling of dangerous gas cylinders, and poses no threat to the environment or the user's health. Stainless-steel instruments and heat-sensitive instruments can be treated simultaneously, which for some users will obviate the need for two separate sterilizers.

The preferred sterilization apparatus in accordance with the invention as illustrated schematically in FIG. 1 includes a sterilization chamber 10 which can be sealed to contain a vacuum. This is achieved with an access door 12, which can be selectively opened for access into the chamber and which seals the chamber in the closed condition. The apparatus further includes an ozone generator 22 for supplying ozone-containing gas to the sterilization chamber, a hydrogen peroxide delivery unit 30 for supplying evaporated hydrogen peroxide to the sterilization chamber 10, and a vacuum pump 40 (CM-005-052 TSO3, Inc.). The vacuum pump 40 is used for the application of a sufficient vacuum to the sterilization chamber 10 to increase the penetration of the sterilizing gas and to be able to generate evaporated hydrogen peroxide solution at a temperature below the temperature inside the sterilization chamber. The vacuum pump 40 in the preferred embodiment is capable of producing a sufficient vacuum in the sterilization chamber to lower the boiling point of water in the chamber below the actual temperature of the atmosphere in the chamber. In the preferred apparatus, the vacuum pump is capable of producing a vacuum of 1 Torr (1.33 mbar). Ozone produced in the ozone generator 22 is destroyed in an ozone catalyst 52 to which ozone-containing gas is fed either after passage through the sterilization chamber 10 or directly from the ozone generator 22 through by-pass valve 29b. The ozone catalyst 52 (AM-004-001, TSO$_3$ Inc.) is connected in series after the vacuum pump 40 to prevent ozone gas escaping to ambient. The ozone decomposing material in the preferred catalyst 52 is carulite. For economic and practical reasons, it is preferred to use a catalyst for decomposition of the ozone in the sterilization gas exhausted from the sterilization chamber 10. The catalyst destroys hydrogen peroxide and ozone on contact and retransforms it into oxygen and water with a certain amount of heat being produced. Catalysts of this type and their manufacture are well known to the person skilled in the art of ozone generators and need not be described in detail herein. Furthermore, other means for destroying the ozone and hydrogen peroxide contained in the sterilization gas will be readily apparent to a person skilled in the art. For example, the gas can be heated for a preselected time to a temperature at which the sterilant decomposition is accelerated, for example, to 300° C. for a period of 3 seconds.

The hydrogen peroxide delivery unit 30 includes a reservoir 220 (AM-213-010, $TSO_3$ Inc.), a metering unit 240, and an evaporator unit 260 (FM-213-003, $TSO_3$ Inc.) directly connected to the sterilization chamber 10 through a conduit 280. (AM-213-003, $TSO_3$ Inc.) The reservoir 220 is equipped with a level sensor 222 to always ensure a sufficiently high level of hydrogen peroxide for the execution of another sterilization cycle. A hydrogen peroxide solution (3-59%) is supplied to the reservoir from a hydrogen peroxide supply unit 200 (see FIG. 7), which will be discussed in more detail below. The hydrogen peroxide solution is supplied into the supply unit 200 from a sealed bottle 180 (see FIG. 7). The evaporated hydrogen peroxide solution produced in the evaporator unit 260 directly enters the sterilization chamber 10 with no intermediate flow restriction or valve. The evaporator unit is preferably equipped with a heating device (not shown) that maintains the temperature of the hydrogen peroxide solution sufficiently high to achieve a higher evaporation rate and prevent freezing of the solution.

The ozone generator 22 (OZ, model 14a, $TSO_3$ Inc.) is of the corona discharge type and is cooled to decrease the ozone decomposition rate, all of which is well known in the art. The ozone generation is associated with energy loss in the form of heat. Since heat accelerates the decomposition of ozone into oxygen, it should be removed as quickly as possible by cooling of the ozone generator 22. The ozone generator in the apparatus is kept at the relatively low temperature of 3 to 6° C. by a cooling system 60, which is either an indirect cooling system with cooling water recirculation, or a direct cooling system with an air cooling unit or a refrigeration unit for cooling (not illustrated). The cooling system is preferably kept at the temperature of 3 to 6° C. In the preferred embodiment, the cooling system is kept at 4° C. so that the ozone-containing gas generated by generator 22 is at the ambient temperature of around 20 to 35° C. Thus, the ozone-containing gas entering into the sterilization chamber for humidification and sterilization is kept at ambient temperatures of 20 to 35° C. This means that ozone decomposition is minimized and the sterilization process is most efficient. The ozone-generator 22 is preferably supplied with medical grade oxygen. Oxygen may also be supplied directly to the sterilization chamber 10 through oxygen supply valve 21. The apparatus can be connected to a wall oxygen outlet common in hospitals or to an oxygen cylinder or to any other source capable of supplying the required quality and flow. The supply of oxygen to the generator 22 takes place across a filter 23, a pressure regulator 24, a flow meter 25 and an oxygen shut off valve 26. The generator is protected against oxygen over pressure by a safety pressure switch 27. The ozone-oxygen mixture generated by the generator 22 is directed to the sterilization chamber 10 through a flow regulator orifice 28 and a mixture supply solenoid valve 29a. The mixture can also be directly supplied to the ozone catalyst 52 by way of a bypass solenoid valve 29b (optional). In a preferred embodiment in which a sterilization chamber of 125 liters volume is used, the pressure regulator 24 and the regulator valve 28 preferably control the oxygen input at a pressure of about 13.8 kPa (2 psig) and a flow rate of about 1.5 liters per minute. However, it will be readily apparent to the skilled person that other flow rates may be used depending on the make and model of the ozone generator 22 and the size of the sterilization chamber.

The vacuum in the sterilization chamber 10 is produced by way of the vacuum pump 40 and the sterilization chamber drainage valve 44.

Valves 29a and 29b are Teflon solenoid valves (CM-900-156, $TSO_3$ Inc.) Valve 26 and vacuum valve 44 are solenoid valves (CM-015-004, $TSO_3$ Inc.).

The preferred ozone generator used in the process and apparatus of the invention is a generator of the corona discharge type, which is well known to the person skilled in the art and need not be further described herein.

Operation

A preferred sterilization method according to the invention includes the following general steps as illustrated by the flow chart of FIG. 3. Articles to be sterilized, such as medical instruments, can be placed directly into the sterilization chamber, but are preferably sealed in sterile packaging containers, sterile wraps or pouches such as generally used in the hospital environment and then placed into the sterilization chamber. Various different types of such containers or pouches are well known to the person skilled in the art and need not be further described herein.

After insertion of the article to be sterilized has been placed into the sterilization chamber in step 320, the door of the sterilization chamber is closed and the chamber sealed in step 340 and a vacuum is applied to the sterilization chamber in step 350 until a first pressure of 1 Torr (1.33 mbar) is reached in the chamber. The sterilization chamber walls have preferably been preheated in a warm-up step 310 to a temperature of 40° C. Evaporated hydrogen peroxide solution is admitted into the sterilization chamber in humidification step 360 to partially sterilize and humidify the chamber contents. The injection of evaporated hydrogen peroxide solution is stopped once a pressure increase of 19 Torr has been achieved in the chamber. The chamber can be maintained sealed for a first exposure period 370 (preferably 2 minutes) during which the hydrogen peroxide at least partially decomposes into free radicals, water and oxygen. Preferably, this exposure period can also be omitted. An ozone containing gas, preferably in the form of a mixture of dry ozone and oxygen is then supplied to the chamber in the ozone injection step 380 and the chamber maintained sealed for a preselected second exposure period 390. No humidification of the ozone containing gas is carried out, or is even necessary, since the chamber atmosphere has been humidified by the hydrogen peroxide solution. Between the application of the vacuum, before the hydrogen peroxide evaporation step, and the end of the second exposure period, all removal of any sterilization atmosphere components is interrupted so that none of the components of the atmosphere are removed before the end of the second exposure period. The steps of vacuum application, hydrogen peroxide injection with first exposure period and ozone gas injection with second exposure period, are preferably repeated at least once, the number of repetitions being determined in step 395 on the basis of the cycle chosen previously in step 330. To remove all remaining sterilants from the sterilization chamber 10 after the sterilization cycle is completed a ventilation phase 400 is commenced, which preferably includes multiple cycles of evacuation of the chamber and flushing with oxygen. After the ventilation phase 400, the door is unlocked in step 410 and the sterilized articles can be taken from the chamber. The temperature of the floor and door of the chamber and of the evaporator unit is preferably controlled throughout the sterilization process.

In an exemplary sterilization apparatus in accordance with the invention, the user has the choice of multiple different sterilization cycles. In a preferred method, the user can choose in cycle selection step 330 of the process among three cycles which have the respective characteristics shown in Table 1 and discussed below.

TABLE I

|  | Cycle phases | | |
| --- | --- | --- | --- |
|  | Cycle 1 | Cycle 2 | Cycle 3 |
| Vacuum | 1 Torr | 1 Torr | 1 Torr |
| Humidification with 50% H202 solution | 20 Torr | 20 Torr | 20 Torr |
| Humidification plateau (optional) | 2 min | 2 min | 2 min |
| 03 Injection | 2 mg/1 | 10 mg/L | 3 mg/L |
| Exposure | 5 min | 5 min | 10 min |
| Nb of repetition(s) | 2 | 2 | 4 |
| Approx. Cycle duration | 46 min | 56 min | 100 min |

Cycle 1 - Surface sterilization of devices having low compatibility with ozone, hinged devices and short flexible endoscopes (1 mm x 85 cm). (Ex. Cameras, cables, paddles, forceps, bronchoscopes, ureteroscopes).
Cycle 2 - Surface devices with high compatibility with ozone, hinged instruments and rigid endoscopes (1 mm x 50 cm).
Cycle 3 - Instruments sterilizable with cycle #1 and complex endoscopes (Ex. gastroscopes, colonoscopes).

Although it is preferred to operate the present sterilization process using a 50% hydrogen peroxide solution, the process can be operated with solutions including 3%-50% hydrogent peroxide. Exemplary conditions for the process when operated with a 3%, 30% and 50% hydrogen peroxide solution are as follows.

TABLE II

| % $H_2O_2$ | Max Injection Pressure (Torr) | Ozone dose (mg/L) | No of repetitions | Conditioning time |
| --- | --- | --- | --- | --- |
| 3 | 44-54 | 25-50 | 2-8 | 2 hrs |
| 30 | 30-44 | 5-25 | 2-6 | 2 hrs |
| 50 | 17-21 (20) | 2-10 | 2-4 | 0 hr |

The maximum injection pressure is the pressure at which injection of the evaporated hydrogen peroxide solution is stopped. The conditioning time represents a time period after sealing of the chamber and prior to application of the vacuum in which the articles to be sterilized are maintained in the sterilization chamber and gradually warm up from room temperature due to the chamber walls, floor and door being heated to about 40° C. This warming up of the load in the chamber is required to prevent undue condensation of water on the load on injection of the evaporated hydrogen peroxide solution. The risk of condensation increases with decreasing hydrogen peroxide solution concentrations.

Once the user has chosen one of the three cycles, the user closes the sterilization chamber door and pushes the start button. The sterilizer control system (see FIG. 9) will then, under the control of a built in operating software, start the sterilization process according to the cycle chosen and using preselected parameters for the cycle chosen. There is no preconditioning of the sterilization load. The cycle starts with the generation a vacuum in the sterilization chamber of approximately 1 Torr (1.33 mbar). An evaporated aqueous hydrogen peroxide solution is subsequently injected into the chamber through the evaporator unit to partially sterilize and humidify the load. Before entering the evaporator unit, the hydrogen peroxide solution passes through the metering unit 240 shown in FIG. 8. The metering unit 240 is directly connected to the evaporator unit 260 and, thus, subjected to the vacuum pressure present in the chamber. The metering unit 240 includes a base block 241 having a passage of a fixed, known volume (not shown) and connected by an intake valve 242 at an upstream end of the passage to the hydrogen peroxide reservoir 220 and by an exhaust valve 243 at a downstream end of the passage to the evaporator unit 260. The flow of hydrogen peroxide solution through the metering unit 240 can be exactly controlled by way of the valves 242, 243, which are switched oppositely and non-overlapping so that one valve is always closed when the other is open and both valves are never open at the same time. In this manner, the passage is evacuated when the exhaust valve 243 is open and the intake valve 242 is closed, filled with hydrogen peroxide solution when the exhaust valve 243 is closed and the intake valve 242 is open and evacuated again when the exhaust valve 243 is again open and the intake valve 242 is again closed. Since the exact volume of the passage is known, the amount of hydrogen peroxide solution supplied per valve cycle is known and the total amount of hydrogen peroxide can be calculated on the basis of the number of valve switching cycles. The number of times and the frequency that the valves 242, 243 open and close are controlled and monitored by apparatus software and can be used to determine the amount of hydrogen peroxide solution removed from the reservoir and to calculate the theoretically remaining amount of solution in the reservoir, based on the total amount aspirated from the supply bottle and the metered amount. The inventors of the present apparatus and method have discovered that, contrary to common general knowledge the exact amount of evaporated hydrogen peroxide supplied into the chamber is not critical. To the contrary, the inventors of the present application have surprisingly discovered that the most reliable determinant of the sterilization efficacy of the hydrogen peroxide vapor is the pressure in the chamber. The sterilization efficacy is dependent on the saturation level of the sterilization atmosphere with hydrogen peroxide. However, the saturation level cannot be calculated reliably from the amount of solution injected, since it greatly depends on the load in the chamber and the adsorption characteristics of the materials in the load. The saturation level is however directly proportional to the pressure in the chamber. Therefore, the saturation level in the chamber can be determined solely on the basis of the chamber pressure rather than by measuring the flow or amount of the injected hydrogen peroxide solution into the chamber. As a result, the number of valve switching cycles during the hydrogen peroxide injection step 360 in an embodiment of the present invention is wholly dependent on the pressure to be reached in the chamber 10 at completion of the hydrogen peroxide injection. In a preferred embodiment, a 50% aqueous hydrogen peroxide solution is used and the pressure increase to be reached in the chamber is 19 Torr. An optional dwell time of 2 minutes follows the reaching of the preset pressure increase of 19 Torr. Then a dose of dry ozone containing gas is injected followed by a second exposure time. The ozone dose depends of the cycle chosen by the user. When the desired number of repetitions of the first and second partial sterilization steps is attained, ventilation of the sterilization chamber 10 is carried out by evacuating and re-filling the chamber 3 times with oxygen in order to remove residuals of the hydrogen peroxide and ozone sterilants.

In order to determine whether a variation in the volume of hydrogen peroxide injected by each pulse during the conditioning phase has an impact on the sterilization effectiveness and on the amount of condensation observed on the load, applicant performed sterilization testing with different injection pulse amounts. Theoretically, the speed of injection/evaporation of the hydrogen peroxide could have an impact on the sterilization effectiveness. By injecting a much larger volume during each pulse, the solution is pushed faster into the chamber, and the time for the liquid to evaporate is diminished. The chance of having more condensation on the instrument or on the packaging material is therefore greater. Condensation that is too pronounced would be expected to create two problems. First, pronounced condensation could limit the ability of ozone to reach the spores at the surface of the instruments. Second, the hydrogen peroxide liquid can stay trapped in the packaging material, being hazardous for people handling the sterilized load afterwards. If the amount of trapped hydrogen peroxide liquid is too large, ventilation of the chamber and packaging at the end of the sterilisation cycle may not be sufficient, to remove all traces of hydrogen peroxide condensate.

When the pressure in the sterilisation chamber is lowered below atmospheric pressure, any liquid present or injected into the chamber will boil at a lower temperature than at atmospheric conditions. In the above described embodiment of the present process, the pressure in the chamber is first lowered and then a volume of hydrogen peroxide is injected in vapour form. The total volume of hydrogen peroxide used is injected in small increments. During injection, the pressure in the chamber increases until a final pressure of 20 Torr (1 Torr starting pressure+19 Torr pressure increase) is reached. Hydrogen peroxide evaporates at a temperature higher than water (50% hydrogen peroxide boiling point is 114° C., and water boiling point is 100° C.). Therefore, the condensate will be more concentrated in hydrogen peroxide than the initial solution entering the chamber. This phenomenon was observed with a UV lamp placed in the chamber. Even if the pressure in the chamber was increasing, the concentration of hydrogen peroxide in vapour read by the UV lamp was decreasing. Also, the concentration of the first hydrogen peroxide droplet (10 Torr) was titrated. It was found that the liquid was approximately 85% concentrated hydrogen peroxide.

At a pressure of about 10 Torr, a layer of micro-condensation of the hydrogen peroxide appeared on objects in the chamber. The thickness of the micro-condensation was calculated to be only a few molecules thick, but can assist the sterilisation, since it is well known that hydrogen peroxide can sterilize in a vapour form as well as in liquid form (Chung et al., 2006; Unger-Bimczok et al., 2008). Also, ozone is more soluble in hydrogen peroxide and can form radicals right at the surface, where spores are present.

In order to inject a high volume at once, a valve separated by Teflon tubing was used instead of the normally used microvalve (TSO3 #: AM-213-001). The tubing length was determined by the volume to be injected. Since the volume contained in the valve is significant, two sizes of valves were used. The first type (TSO3 #: CM-900-157) with an orifice of 0.062", was used for a volume up to 1.5 mL. The second Neptune type, with an orifice of 0.156", (TSO3 #: CM-900-156), was used for a volume up to 3.5 mL. The larger valve size also helps to push the large liquid volume into the chamber. For the 35 µL volume, a Burket 7616 micropump (TSO3 #: CM-113-001) was used. For the 23 µL volume, a larger, specially-made block was used.

Two cycles were used for this experiment. To test the sterility, Cycle 1 (half-cycle) was used, where the injection step of the conditioning phase was modified with a variation in volume and pulse for each attempt, as previously described. As for the condensation effect, Cycle 3, consisting of four phases, was utilized. This cycle was chosen due to the fact that a greater quantity of hydrogen peroxide was injected for the cycle, making it the worst case scenario. A third test was performed for sterility testing. Lumens (Teflon 1 mm×80 cm) were inoculated using the wire technique according to MCB-09-A07. After exposure to a half-cycle of Cycle 1, the sterility of each lumen was determined according to MCB-09-A04 rev. 7 by quantitative recovery using the ultrasound technique followed by filtration.

A burette was plugged onto the valve system in order to precisely determine the injected volume. This volume was then divided by the pulse number. The three TSO3 cycles were tested with a special load representing an average load for these three cycles. The load was always at room temperature at the beginning of the cycle. A UV lamp was also installed on the sterilizer used. This allowed analysis of the hydrogen peroxide vapour during the conditioning phase Sterility was verified with Teflon wires (1 mm×80 cm) inserted into the tubing, and tested in a half-cycle of Cycle 1. The first injected volume by each pulse during the conditioning phase was 1.5 mL. In the case of a good result for sterile efficacy, the volume would be doubled. If the result was not satisfactory, then half the volume would be tested. Since the result for the test using 1.5 mL per pulse was good, the test was repeated with 2.5 mL and 3.4 mL. Testing was stopped at 3.4 mL injection because only two pulses were necessary to reach the desired pressure of 18 Torr. The normal conditioning phase stopped at 19 Torr, but to ensure the pressure was not exceeded, the microvalve was used between 18 to 19 Torr.

Sterility was achieved with 3.4 mL (all tests were at zero for spore count). Thus, applicant found that variations in pulse volume have no effect on sterilization efficacy. However, it was noticed during the sterility testing that condensation was present exactly where the hydrogen peroxide is injected into the chamber. Therefore, more tests were performed in order to determine the maximum volume that could be injected by each pulse without condensation.

The first volume injected was again 1.5 mL. Condensation was present on the load at the injection site. The amount of liquid condensate measured was similar to that observed with a 3.4 mL injection pulse. The pulse amount was then gradually decreased by reducing the injected amount by half each time until no more condensation was visible. At 75 µL, condensation was again similar to that with an injection pulse of 3.4 mL. A significant reduction in condensation build up was observed below a pulse volume of 75 µL. At 35 µL, condensation was still visible but much reduced. At 23 µL, almost no condensation was visible. At a pulse volume of 16 µL absolutely no condensation was observed. Condensation was found to occur at pulse volumes above 20 µL. Thus, to control the amount of unwanted condensation of hydrogen peroxide, it is preferred to use a pulse injection volume of less than 75 µL, more preferably below 35 µL, most preferably about 20 µL.

In an exemplary process in accordance with the invention, the sterilization chamber walls are maintained at a temperature of 40° C. while the load temperature may vary between 20° C. and 25° C. The concentration of the hydrogen peroxide solution used is preferably 50%, but, concentrations as low as 3% and as high as 59% can be used. The pressure reached inside the chamber is a function of the hydrogen peroxide concentration used (see Table II). Even though the pressure reached is the same for each cycle discussed above, the volume of hydrogen peroxide solution required depends on the concentration of the solution, the type of load in the chamber and the hydrogen peroxide adsorption capacity of the load. The humidification level in the sterilization atmosphere prior to ozone injection can be adjusted by using different concentrations of the hydrogen peroxide solution.

The dose of ozone varies between 2 mg/l for cycle #1 and 10 mg/l for cycle #2 and its exposure time varies between 5 minutes for cycle #1 and 10 minutes for cycle #3.

The amounts of ozone used in prior art sterilization processes employing humidified ozone as the sterilization gas are generally about 85 mg/l. Using hydrogen peroxide for partial sterilization as well as humidification of the load prior to ozone injection allows for a significant reduction in the amount of ozone required for achieving sterilization (SAL $10^{-6}$) down to a dose between 2 mg/l and 10 mg/l, depending on the cycle chosen. This reduction is much higher than would be expected from just the fact that hydrogen peroxide and ozone are used in the same sterilization cycle.

Indeed the evaporated hydrogen peroxide solution injected into the chamber is not sufficient to achieve sterilization, although a 4 log reduction in spores has been observed. However, adding only a very minor amount of ozone in the range of 1-10 mg of ozone per liter of sterilization atmosphere results in full and complete sterilization at the level required under the Security Assurance Level standards of the FDA or world standards, such as ISO (SAL $10^{-6}$). Such complete sterilization could not be achieved using only the injection of evaporated hydrogen peroxide solution, independent of the amount of hydrogen peroxide solution used and the concentration of the solution. Moreover, high concentrations of hydrogen peroxide reduce compatibility with some instruments. In addition, a longer dwelling time after hydrogen peroxide injection, for example 3 minutes instead of 2 minutes, does not enhance sterilization efficacy. In fact the dwelling time after hydrogen peroxide injection appears to have no effect on sterilization efficacy. Yet, adding only the minor amount of ozone as discussed above surprisingly leads to complete sterilization.

During the evacuation step 350 (see FIG. 3), oxygen supply valves 21 and 26, mixture supply valve 29a, and mixture bypass valve 29b are closed and the chamber drainage valve 44 is opened. The sterilization chamber 10 is evacuated to a vacuum pressure of about 1 Torr (1.33 mbar). Once this pressure is reached, which is determined by way of a pressure sensor 13 on the sterilization chamber, the chamber drainage valve 44 is closed and the metering unit 240 activated to supply hydrogen peroxide solution to the evaporator unit 260 in which the solution is evaporated and subsequently flows freely into the sterilization chamber 10. Once a pressure increase of 19 Torr is reached in the sterilization chamber 10, as determined by pressure sensor 13, the metering unit 240 is deactivated and the supply of hydrogen peroxide solution to the evaporator 260 is stopped. The chamber can be maintained sealed so that no injection of any substance occurs during a following first exposure period 370, which may lasts for 2 minutes. However, that exposure period is completely optional. Shortly before the end of the hydrogen peroxide injection step 360, (usually about 2 to 6 min.), the ozone generator is activated to ensure a supply of ozone containing gas. The flow of the oxygen/ozone mixture exiting the ozone generator is controlled at all times by regulator orifice 28 capable of resisting the vacuum and of adjusting the flow to between 1 and 3 liters per minute. Activation of the ozone generator 22 includes opening of supply valve 26 and mixture bypass valve 29b. Supply valve 26 lets oxygen enter the generator. The ozone-oxygen mixture produced by the generator is then guided directly into the ozone catalyst 52 through mixture bypass valve 29b. After completion of step 370, the oxygen-ozone mixture produced by the generator 22 is guided into the sterilization chamber 10 by opening the mixture supply valve 29a and closing the mixture bypass valve 29b. The oxygen-ozone mixture enters the chamber 10 until the desired ozone concentration according to the cycle chosen is reached in the chamber. The time required for this step is dependent on the flow rate and concentration of the ozone gas in the mixture (preferably 160 to 200 mg/l NTP), as determined by an ozone monitor 15 of a type well known in the art. Once the desired concentration is reached, the mixture supply valve 29a is closed to seal off the sterilization chamber and to maintain the ozone/oxygen gas mixture in the chamber under vacuum.

Once the supply of the sterilization gas (mixture of oxygen and ozone gas) into the chamber is stopped, the generator 22 is stopped and the oxygen supply valve 26 is closed. The chamber is maintained sealed for an exposure period of 5 to 10 minutes, depending on the sterilization cycle chosen by the user. Also dependent on the cycle chosen, steps 350 to 390 are repeated 1 to 3 more times before the sterilization is complete. This set-up conformed to the Security Assurance Level standards of $10^{-6}$ (SAL $10^{-6}$).

To remove all remaining hydrogen peroxide, ozone and humidity in the sterilization chamber 10 after complete sterilization, the ventilation phase 400 is engaged. The ventilation phase begins after the last exposure period 390. The chamber drainage valve 44 is opened and a vacuum is applied down to approximately 6.5 mbar. Once the vacuum pressure of 6.5 mbar is obtained, drainage valve 44 closes and the oxygen supply valve 21 opens, admitting oxygen into the sterilization chamber 10. Once atmospheric pressure is reached, the oxygen supply valve 21 is closed, the sterilization chamber drainage valve 44 is opened, and vacuum reapplied until a pressure of 1.3 mbar is reached. This last ventilation cycle, down to 1.3 mbar, is repeated once for a total of three ventilation cycles. Once atmospheric pressure is reached after the last cycle, the door mechanism of the sterilization chamber is activated in step 410 to permit access to the contents of the sterilization chamber. The ventilation phase has two functions. First, to remove all sterilant residues in the sterilization chamber before opening the access door and, second, to dry the sterilized material by evaporation when the vacuum pressure is applied. Of course, different vacuum pressures, cycle times and number of repetitions can be used, as long as the desired sterilant removal and drying are achieved.

The sterilants and humidity containing gas evacuated from the sterilization chamber 10 is passed over the catalyst 52 prior to exhausting the gas to the atmosphere to ensure a complete decomposition of the sterilants. The catalyst 52 is used during only two portions of the sterilization cycle, the activation of the generator 22 (with valves 26 and 29b) and the evacuation of the sterilization chamber 10. During the start up phase of the generator 22, the mixture bypass valve 29b is opened and the ozone is guided across the catalyst 52. Once the start-up phase of the generator 22 is complete, the bypass valve 29b closes. During ventilation of the sterilization chamber 10, the sterilization chamber drainage valve 44 is opened and the ozone containing sterilization waste gas is guided to the catalyst 52. Once the evacuation of the sterilization chamber 10 is completed, the drainage valve 44 is closed. The circulation of ozone is ensured by the vacuum pump 40. The catalyst 52 can be located upstream or downstream of the vacuum pump 40.

In effect, at 20° C., water boils up to an absolute pressure of 23.3 mbar and at 35° C., water boils up to an absolute pressure of 56.3 mbar. The vacuum in the sterilization chamber is preferably adjusted at a pressure where the boiling temperature of water is lowered below the temperature in the sterilization chamber. That boiling temperature may be so low that the temperature of the hydrogen peroxide solution in the evaporator unit would decrease rapidly and, depending on the energy available from the surrounding structure, may freeze if no energy supply is provided. The energy needed to evaporate the hydrogen peroxide solution is taken from many sources. It is taken principally from the main body of the evaporator unit 260, which is in the form of an aluminum block provided with a heating arrangement (not shown). The evaporation process may also cool the humidifier to a point where moisture condenses on the sterilization chamber walls. This is avoided by heating the chamber walls sufficiently to keep them at least at room temperature, preferably at 40° C. This is achieved with a heating arrangement (not illustrated), which will be readily apparent to the person of skill in the art.

The evaporated hydrogen peroxide solution injected into the chamber increases the relative humidity in the sterilization chamber. This humidification significantly improves the efficacy of the ozone sterilization step. Oxygen/ozone-containing sterilization gas is injected into the humidified sterilization chamber at a temperature close to ambient. The ozone-containing gas is not heated prior to injection.

Hydrogen peroxide has its limitations when it comes to sterilizing medical instruments. H2O2 is less stable when in contact with metal, as for example, stainless steel. This problem is aggravated at low pressures, at which chemical reactions are accelerated. Therefore, the decomposition of hydrogen peroxide will be accelerated under vacuum, limiting the time available to sterilize long metal tubing. Moreover, the diffusion of H2O2 is limited since it is not a gas. Hydrogen peroxide would reach the end of long tubing by way of diffusion, but by that time its concentration will have decreased, due to accelerated decomposition, to a level where it is no longer sufficient for sterilization.

Applicants have discovered, as disclosed above, that these problems can not only be overcome by the addition of a sterilant gas such as ozone, but that the humidification of the chamber by decomposition of the hydrogen peroxide into free radicals improves the efficacy of the sterilant gas. Moreover, applicants have surprisingly discovered that ozone can be advantageously replaced by nitrogen monoxide, or nitric oxide. The applicants discovered that the water and oxygen generated during hydrogen peroxide decomposition also improves the efficacy of the nitric oxide.

Nitrogen monoxide (or nitric oxide) is known to be cell toxic at low concentrations. In the presence of water and oxygen, NO reacts to form nitrogen dioxide, NO2, which is also highly toxic. In the absence of oxygen, NO does not form NO2, but reacts to form nitric acid, which is very corrosive to other materials.

$$2NO+3H2O2 \rightarrow 2HNO3+2H2O \quad (1)$$

$$2NO2+H2O2 \rightarrow 2HNO3 \quad (2)$$

The problem of nitric acid formation is minimized by mixing the nitric oxide with hydrogen peroxide instead of water, since the required NO concentration after hydrogen peroxide pre-conditioning is very low. H2O2 treatment, weakens the spore coat, and hydrogen peroxide and nitric oxide, when mixed together, form free radicals, similar to the reaction of ozone when mixed with hydrogen peroxide.

$$HO+H2O2 \rightarrow H2O+HO2. \quad (3)$$

$$HO2.+NO \rightarrow HO.+NO2 \quad (4)$$

$$HO.+NO \rightarrow HONO \quad (5)$$

Those radicals will react rapidly with all organic substances, oxidizing them. The speed of oxidation will be in the order of 109, instead of 101 for NO or O3 alone.

Applicants tested the efficacy of replacing the ozone gas originally tested by another gas, such as oxygen and nitric oxide. The test evaluated the sterile efficacy on inoculated devices. Inoculated wires were inserted in tubing and afterwards in pouches. The pouches were also placed at the top of the loading carriage in the sterilization chamber. This area is considered the point of least efficacy in the chamber.

EXAMPLES

The same loads were used for the three series of tests performed: ozone, oxygen and nitric oxide. The length, diameter, material and type of tubing were different for each cycle and are described in Table 3. The inoculated lumens were placed in a special load representing an average load for the three cycles.

TABLE 3

Length, diameter and material of tubing for each cycle.

| Cycle number | Diameter (mm) | Length (cm) | Material |
| --- | --- | --- | --- |
| Cycle 1 | 1 | 80 | Teflon |
| Cycle 2 | 1 | 50 | Stainless steel |
| Cycle 3 | 1 | 110 | Teflon |

The lumens used to evaluate the sterile efficacy were inoculated according to protocol MCB-09-A07 rev 9. The wire method was used. The wires were inoculated with 10 µL of a *G. stearothermophilus* ATCC 7953 spores suspension of $1.0 \times 10^6$ to $2.5 \times 10^6$ UFC/10 µL. The inoculated wires were left to dry overnight at normal room conditions.

Test loads were exposed to a half-cycle of each cycle. For the experiment with oxygen and nitrogen oxide, ozone was replaced by the gas to be tested. A burette was also plugged on the valve system in order to precisely determine the H2O2 injected volume. After the exposure, the sterility of each lumen was determined according to MCB-09-A04 rev. 7 by quantitative recovery using the ultrasound technique followed by filtration.

Ozone

The baseline of sterile efficacy on the inoculated lumens used in each cycle was established using only hydrogen peroxide. Cycles using hydrogen peroxide and ozone were performed to compare the efficacy of oxygen and nitrogen oxide to ozone.

Oxygen

The oxygen was injected in the chamber using the same system as that used for ozone. The ozone generator was turned off.

Nitric Oxide

The NO was injected however directly in the chamber from an independent NO cylinder (Praxair). A Neptune valve with an orifice of 0.156" (TSO3 #: CM-900-156), separated by a Teflon tube was used for this injection. By doing so, the gas was forced into the chamber.

All tests were performed outside in order to limit possible dangers from accidental leaks. A NO detector was used. A long tube was plugged into the catalyst converter unit, to allow the NO to be eliminated far from the set-up. A calculation was performed (see below) to determine the number of valve injections necessary to obtain a concentration of 2 mg/L.

Valve volume: 3.3 mL (Volume calculated in R-1937)
NO Density NTP: 1.25 g/L
Sterilisation chamber volume: 125 L
Finale concentration desired: 2 mg/L
NO Pressure: 3 psig
Corrected volume: $3300 \times ((14.7+3)/14.7) = 3973.2$ µL
Mass to be injected: $0.002$ g/L $\times 125$ L $= 0.25$ gno Masse injected by each injection: 1.25 g/L×0.003974 L=4.9665×10⁻³ g/injection Number of injections required: 0.25 gno/4.9665×10⁻³ g/injection=50 injections Two lenses were present in the chamber, one at the bottom rear, and the other one at the top rear. They were exactly aligned one on top of the other. One lense emitted UV light from a tungsten source, and the other lense was connected to a UV detector. This set-up allowed the measurement of the hydrogen peroxide vapour in the chamber.

Hydrogen peroxide has some inactivation activity against spores of *G. stearothermophilus*. However, the percentage of sterility achieved in lumens is not sufficient to use it alone, especially for rigid and long flexible lumens. Results for hydrogen peroxide and of other gases mixed with the hydrogen peroxide are summarized in Table 4.

TABLE 4

Percentage of sterility for the three $TSO_3$ cycle with different sterilizing agent mixed with hydrogen peroxide.

| Sterilizing Agent Used | Sterile lumens | | |
|---|---|---|---|
| | Cycle 1 | Cycle 2 | Cycle 3 |
| $H_2O_2$ | 50% | 12.5% | 16% |
| $H_2O_2 + O_3$ | 77% | 50% | 77% |
| $H_2O_2 + O_2$ | 11% | 0% | 77% |
| $H_2O_2 + NO$ | 100% | 66% | 66% |

In the case of oxygen mixed with hydrogen peroxide, concentrations equivalent to the ozone dose were used in each cycle, in other words, 2 mg of O2/L for cycle 1, 10 mg/L for cycle 2, and finally 3 mg/L for cycle 3. Oxygen hindered the efficacy of the process in Cycles 1 and 2 compared to hydrogen peroxide alone or mixed with ozone. In Cycle 3, the efficacy of the process with oxygen or ozone is equivalent. Consequently, oxygen was found ineffective to replace ozone.

Although nitric oxide is a well known disinfecting agent, it was never mixed with hydrogen peroxide, since the mixture can be explosive at high concentrations. To minimize the explosion danger, the NO concentration was limited to 2 mg/L for three cycles of a first series of tests. Sterility was achieved for some samples in all of the cycles so the nitrogen monoxide concentration was not further increased. The results were very conclusive, i.e., better than or similar to ozone mixed with hydrogen peroxide.

Even if no controls were done to verify the inactivation of *G. stearothermophilus* spores by NO in this study, it was demonstrated in multiple studies that the inactivation rate of NO is low. When NO is injected into a sterilization chamber and combined with humid air, the NO reacts with the oxygen at a predictable rate to form NO2, which is lethal to the spores of *G. stearothermophilus*. When NO is injected into a sterilization chamber with no oxygen atoms present, the NO does not form NO2, and spores are not sterilized (http://www.m-ddionline.com/article/sterilizing-combination-products-using-oxides-nitrogen). Based on the Noxilizer sterilization process publisher data, at 5.12 mg/L NO2, the D-value is only 0.3 minutes. At 3 mg/L, the D value is approximately 1.9 minutes.

In this experiment, the amount of NO injected was 2 mg/L. Considering that all NO molecules were transformed in NO2, a D-value of 1.9 minutes for a concentration of 2 mg/L of NO2, only 2.5 log of spores would have been inactivated by the NO2. This less than the 6 log present on the inoculated devices. In reality, the conversion rate of NO in NO2 is probably not 100%, and the D-value is more than 1.9 minutes. Thus the number of spores inactivated by NO only is probably more around 1 log.

The substitution of ozone by another gas was tested in all three cycles of the present process. Hydrogen peroxide injection was performed as usual. Two gases were tested. The first, oxygen, did not achieve conclusive results. Sterility was not achieved in two of the three cycles.

Nitric oxide was also tested. Results show a complete sterility in all three cycles. The concentration used for all tests was low. Only 2 mg/L was injected for the three tests. The use of this chemical could be considered in the future. However, significant changes to the sterilizer will have to be made to accommodate this. Since $NO_2$ is formed during the cycles, only compatible materials could be used Also, protective equipment, like for example NO detector would have to be considered.

Other sterilant gases that can interact with hydrogen peroxide to continue the formation of free radicals could be used in replacement of ozone, such a chloride dioxide.

On the other hand, many different molecules can have the same effect as hydrogen peroxide on ozone. Some ions can also have the catalytic effect of hydrogen peroxide on ozone. $Co^{2+}$, $Ni^{2+}$, $Cu^{2+}$, $Mn^{2+}$, $Zn^{2+}$, $Cr^{2+}$ and $Fe^{2+}$, $Ti^{2+}$ ions enhance the decomposition of ozone (Ahmed et al., 2005). All transition metals that can form a molecule with oxygen will decompose ozone. The positive ions will try to become neutral by taking an oxygen atom to the ozone molecule. The ozone molecule being more or less stable will easily give the oxygen atom. Water with a basic pH will be richer in hydroxyl ions. Hydroxyl ions decompose ozone into atomic oxygen. Those oxygen atoms can form hydroxyl radicals afterward. Therefore, any molecules that can be used to render the solution pH basic will favour the decomposition of ozone. Good examples are NaOH or KOH.

Another source of hydroxyl radicals are all solvents containing an alcohol group. Those solvents will provide OH ions and will favour the dilution of ozone. In the same vein, formate and humic substances can initiate the chain towards radical formation (Glaze et al., 1987). Some acids can also be used such as acetic acid and para-acetic acid. Ozone being more soluble and stable in acidic solution will be able to react longer and be more concentrated. Any molecule containing a carbonate, bromine, phosphate or sulphate group will also decompose ozone (Beltran, 2004).

Figure 2:
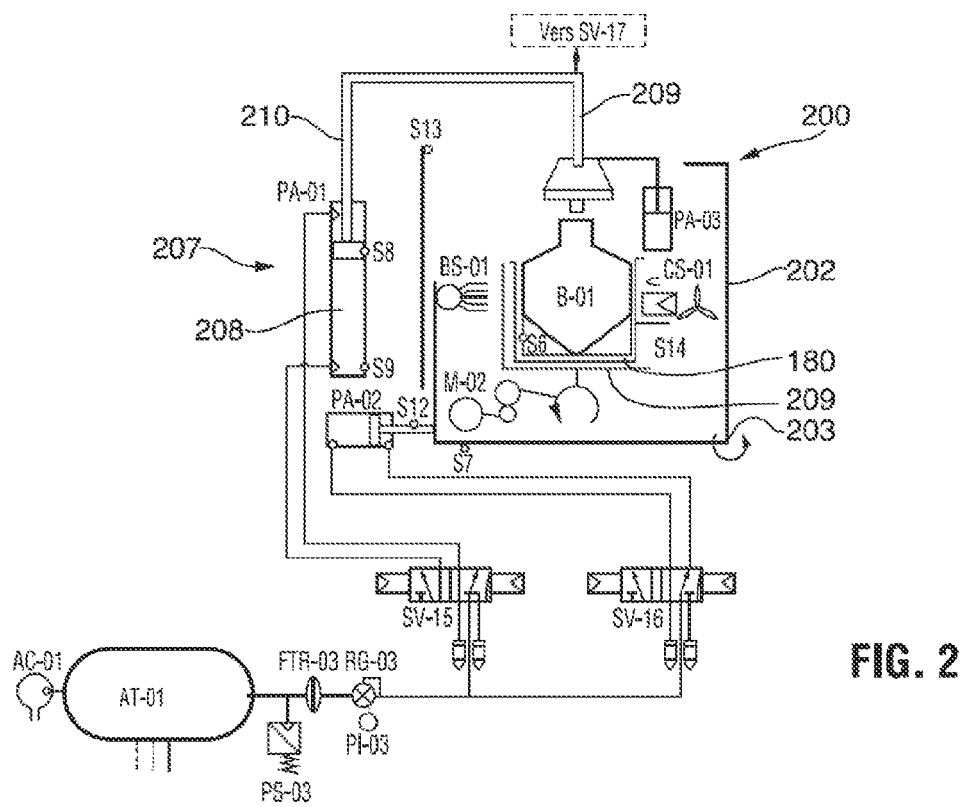
FIG. 2 shows a schematic diagram of a hydrogen peroxide delivery system in accordance with the invention, the illustrated parts of the system being listed in Table III.
Figure 7:
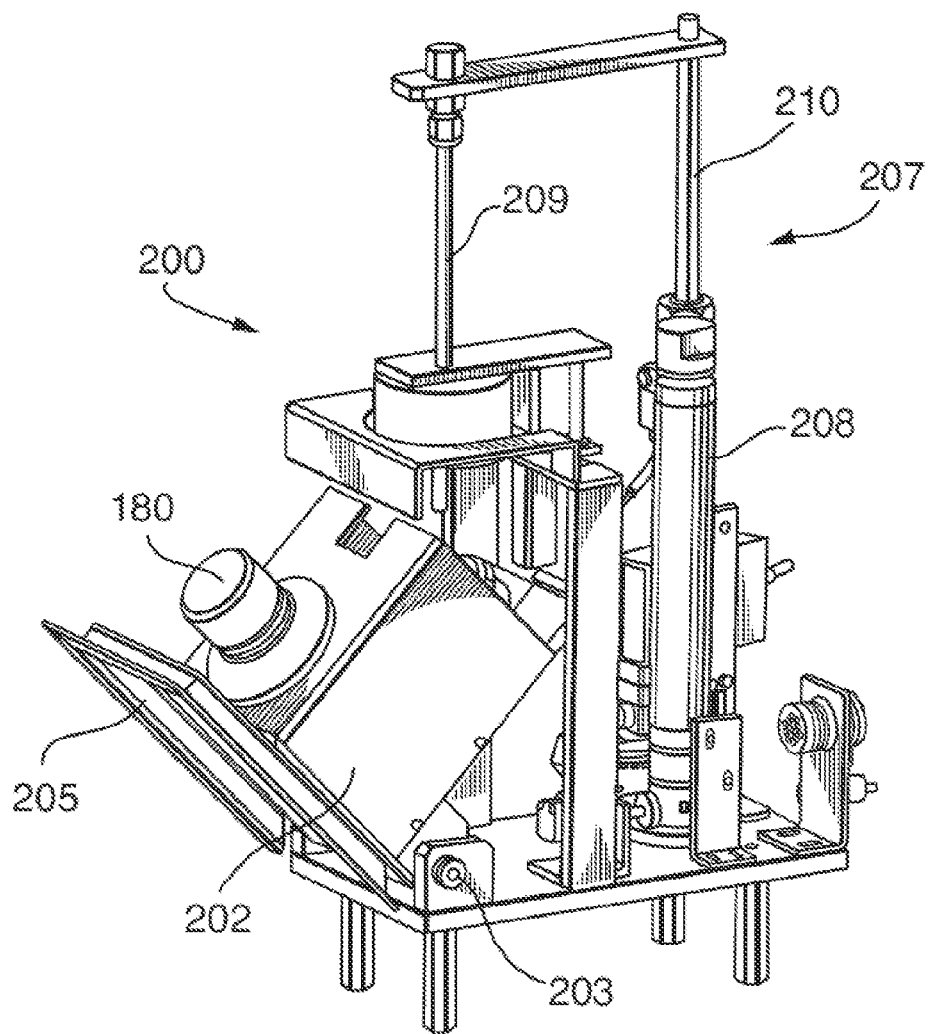
FIG. 7 shows an exemplary embodiment of a hydrogen peroxide supply unit in accordance with the invention.

As shown in FIGS. 2 and 7, the delivery unit 200 includes a bottle holder 202 for receiving a sealed hydrogen peroxide solution bottle 180. The holder has a bottle seat 204 in which the bottle 180 is fittingly received. The bottle 180, which will be discussed in more detail further below, is held in the seat 204 by gravity only. The holder 202 is rotatably mounted on pivot 203 for movement between an open position as illustrated in FIG. 7, which the bottle 180 can be placed into or removed from the holder and a closed position in which the holder is completely within the sterilizer cabinet (not shown) and a front cover 205 of the holder closes off all access to the holder from outside the cabinet. When the holder 202 is in the closed position, a pneumatically driven drainage arrangement 207, including a needle drive, in this embodiment a vertically oriented pneumatic cylinder 208, and a drainage needle 209 mounted on the piston rod 210 of the cylinder, is activated to drain all hydrogen peroxide solution from the bottle 180. This is achieved by activating the cylinder 208 to force needle 209 through the bottle seal until the needle tip reaches the bottom of the bottle 180. The needle 209 is fluidically connected to the reservoir 240 (see FIG. 8) and the solution is aspirated from the bottle 180 and into reservoir 240 by using the vacuum generated by the vacuum pump 44 to which the reservoir 240 can be fluidically connected by conduit 211 and valve 212 (see FIG. 1). Once the contents of the bottle 180 have been aspirated, the holder can be opened and the bottle removed, or the empty bottle can be kept in the holder until a refill of the reservoir 240 is required. The reservoir 240 is provided with a level sensor 242 which provides a signal to the control system on the liquid level in the reservoir. Based on the signal received from the sensor 242, the control system notifies the user if the amount of liquid in the reservoir 240 is insufficient for the execution of the cycle selected by the user.

In an alternate embodiment, the hydrogen peroxide delivery system does not include a reservoir. Instead, the bottle 180 itself is cooled down (CS-01) to avoid rapid degradation of the aqueous hydrogen peroxide. A sensor (S14) measures the amount of solution left in the bottle. When the solution reaches a $1^{st}$ preselected level, a $1^{st}$ warning appears on the screen and when a lower, $2^{nd}$ preselected level is reached, the message generated from the software to the operator specifies that only one more sterilization cycle #1 or #2 can be run with the remaining solution in the bottle. The operator will then have to reload the delivery system with a fresh, full bottle.

As shown in FIGS. 10a to 10d, the bottle 180 has a conical bottom 182 to ensure a complete drainage of all liquid in the bottle, thereby reducing the danger of spills or contamination on removal of a drained bottle. In order to ensure the bottle 180 securely remains upright, a stand 184 is attached to the bottom end of the bottle. The stand 184 includes an upturned cup 185 snap fitted into a circumferential groove 186 on the bottle exterior wall 187. The needle 209 is aligned with the lowest point in the bottle bottom and can be moved into the bottle, through the bottle seal, until it reaches the lowest point in the bottle. Mechanical, electronic or other control structures and functions are provided to ensure contact of the needle with the bottle bottom while preventing penetration of the bottle bottom. A pressure sensor is preferably incorporated into the reciprocating needle drive and/or the needle mount (not shown).

Control System

Figure 9A:
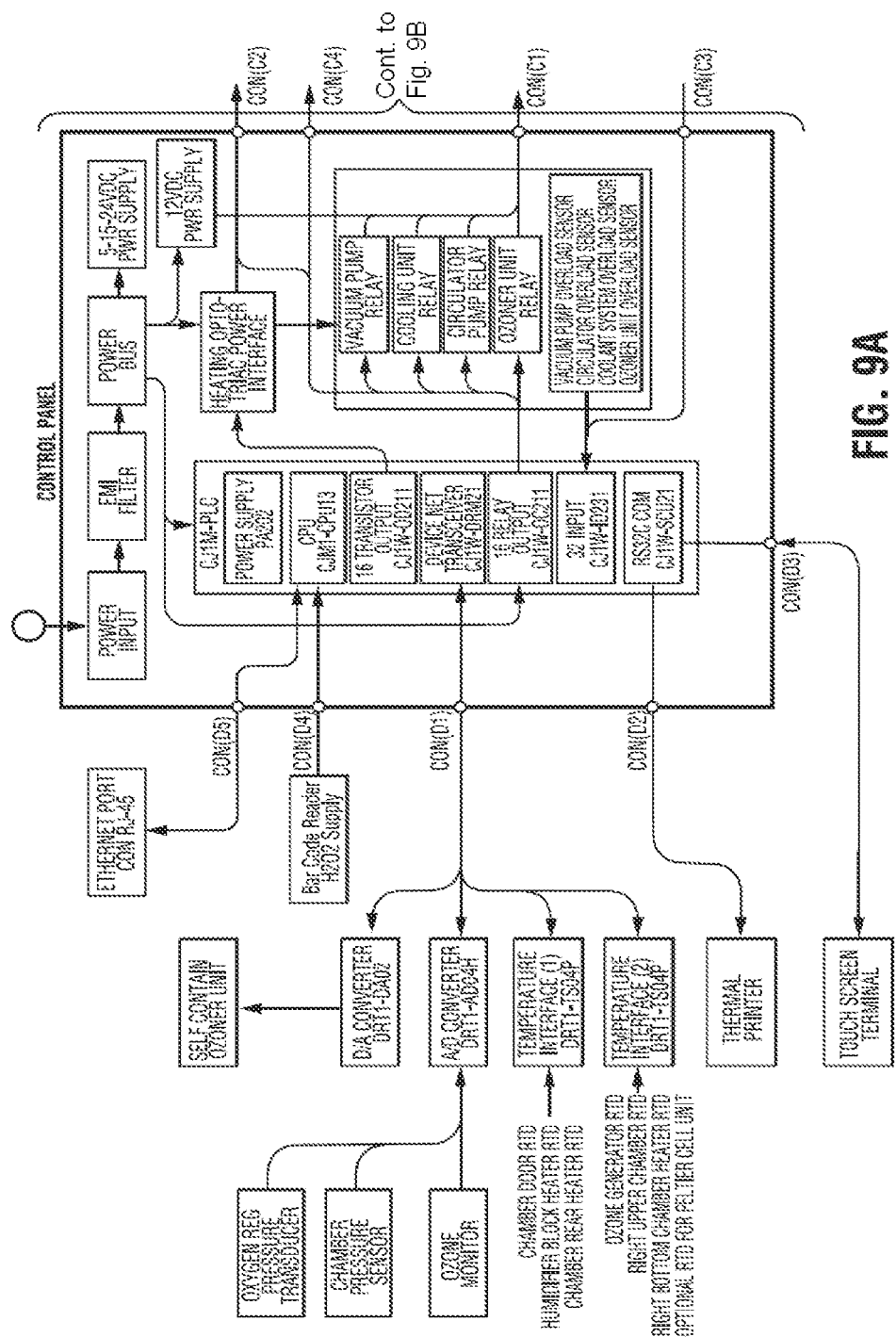
FIG. 9 is a schematic diagram of a control system for an apparatus in accordance with the invention.
Figure 10A:
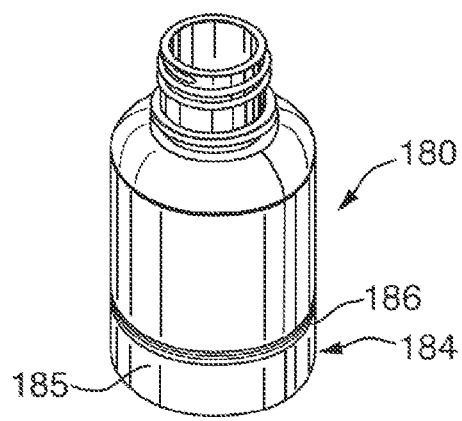
FIG. 10a is a perspective view of a sterilant container in accordance with the invention.
Figure 10B:
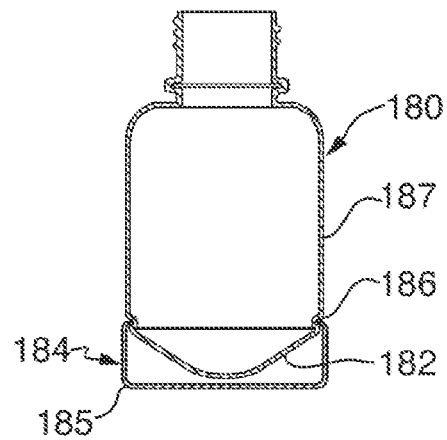
Figure 10C:
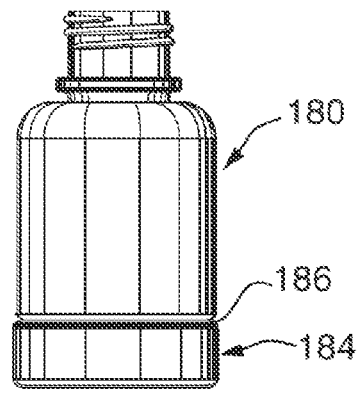
Figure 10D:
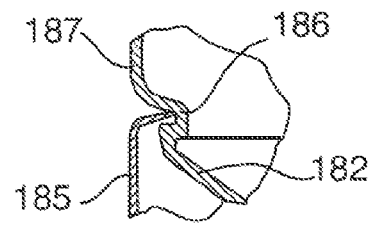
FIG. 10d is enlarged detail B of the container shown in FIG. 10b.

The sterilization apparatus is preferably controlled by the scheme presented in the electrical block diagram (FIG. 9 and Process Flow Diagram (FIG. 3). The control system is built around a PLC shelf (Programmable Logic Controller). This shelf contains a power supply (107) a CPU unit (108), a Device Net Transceiver (109), a 32×24 Volt DC discrete input module (110), a 16×120 VAC discrete output module (111) and finally 16 transistor discrete output module (112), an RS232C communication module. All those modules are stacked together by an intrinsic connecting system that contains a data and address bus.

Device Net is an industrial serial communication protocol largely used in the industry for instrumentation and control. In this sterilization apparatus, the Device Net transceiver (109) is used to communicate in full duplex, the data between the CPU (109) and the 15 bit A/D converter (106), a 15 bit D/A converter (125) and both Digital Temperature Interfaces (120), (121).

The PLC CPU possesses three RS232 ports. One is used to receive and send data to the Touch Screen Terminal (118), another one is used to send data to a thermal printer (119) and the last port is used as a service port where a PC (Personal Computer) can be hooked up to communicate with the PLC CPU (108) to load up the control protocol program. (Control Protocol Program is not in the scope of this document).

The Touch Screen terminal (118) is located at the front of the sterilizer beside the thermal printer (119). Touch Screen Terminal and thermal printer constitute a User Interface terminal.

Power needed for: "thermal printer (119), Device Net Link, (109), (106), (120), (121), (125), Chamber Pressure Sensor (104) electronic oxygen regulator (126) and PLC discrete inputs (111) and discrete outputs (112" is provided by the DC Power Supply (103).

Chamber Pressure Sensor (104) and Ozone Monitor (105) have a standard 0 to 10 VDC output signal. Electronic Oxygen Regulator have an ouput of 0 to 5 VDC. All signals are sent to a 15 bits A/D converter. All converted signals are sent to the CPU by the Device net digital link for processing.

Power input (100) of the sterilizer is a three wire 208 to 240 VAC single phase type without neutral. The power input is filtered to prevent conducted RFI (101). The power is distributed by power distribution buss (102) to the various electrical systems of the sterilizer apparatus.

A cooling system (60) is used to cool down the ozone generator. This system includes the cooling unit (114) and the coolant circulator pump (113). The temperature of the coolant in the generator is sensed by an RTD located at the generator. The temperature is sent to the CPU (108) by the Device Net system (109) (120) (121). Coolant circulator (113) and cooling unit (114) are controlled by contactors driven by PLC outputs (111) which in turn are controlled by the software protocol. All input and output required to achieve cooling system control are listed on the electrical block diagram as: Circulator Pump Relay, Cooling System Relay, Circulator Overload Sensor, Cooling System Overload system, Refrigerant Low Pressure and Coolant Flow Switch.

The vacuum control system includes the vacuum pump 40 and a pressure sensor 104. The start and stop operations of the vacuum pump are controlled according to the control protocol. All input and output required for the vacuum system is listed on the diagram: Vacuum Pump Contactor, Vacuum Pump not running sensor, Vacuum pump Overload sensor, Vacuum to Chamber Valve (44), Air Pulse Valve (18) and Oxygen to Chamber Valve (21). The pressure sensor output is converted by the 15 bit A/D converter (106) and sent to the CPU by the Device Net digital Link (109). The pressure sensor also possesses two discrete outputs indicating to the CPU (108) the following conditions: Chamber Pressure Sensor at Temperature and Chamber Pressure Sensor Heater failure. Those two signals are listed on the electrical block diagram as PLC inputs.

The sterilization chamber door actuator system includes an electric drive of the screw type and four inductive sensors which allow the detection of the closure of the door and the locked or unlocked position of the actuator as part of the control protocol. The door opening system is also used in the alarm conditions management protocol to assure the safety of the user. All input and output required to achieve the door actuator system are listed on the electrical block diagram as: Lock Door Relay, Unlock Door Relay, Door closed Lower Sensor (S2), Door closed Upper Sensor (S1), Door Locked Sensor (S4) and Door Unlocked sensor (S3).

The Ozone power supply (116) includes a full wave rectifier, an oscillator circuit and a high voltage transformer. The output of the transformer is hooked up to the ozone generator (22). The power supply (116) is mounted as a resonator using the non-ideal characteristics of the high voltage transformer. The CPU 108 controls the ozone production and ensures by way of the ozone monitor 104 and Electronic oxygen regulator (126), that the concentration desired for sterilization is achieved and maintained throughout the sterilization cycle.

All input and output required by the Ozone Generation System is listed on the diagram as: Oxygen Supply Valve (26), Ozone to Chamber Valve (29a), Ozone Dump to Catalyst Valve (29b), Ozone Monitor Zeroing), High Voltage Standby Relay, High Voltage Current Limiter, Ozone High Voltage Overload sensor Rectifier High Temperature Sensor, Ozone monitor Failure.

The oxygen supply system is a unit called Electronic Oxygen Pressure Regulator. A proportional Valve (26) which also shuts off the oxygen is controlled by an integrated PID circuit converting an analog signal from an absolute pressure sensor (27). Then the PID sends the appropriate duty cycle current to the proportional valve (26). With the orifice 28 this system constitutes an oxygen flow regulator. The mechanical regulator 24 is used as a first stage regulator to lower the oxygen pressure of 60 psi to 10 psi. The electronic regulator also provides the alarm condition protocol to ensure the protection of the user. Inputs used for the alarm condition are listed on the electrical block diagram as: Oxygen High Pressure Sensor and Oxygen Low Pressure Sensor. Also, the electronic oxygen pressure regulator provided a 0 to 5 VDC analog output read by the A/D converter 106 trough device net network.

The control system is provided with a user interface 118. In the preferred embodiment, this interface includes a touch-sensitive liquid crystal display (LCD) screen 118, a printer 119 for performance reports and a communications port 153 (Series RS-232) allowing the user to receive and transmit information necessary for use of the apparatus. It will be readily apparent to the person skilled in the art that other types of user interfaces can be used such as touch-sensitive pads, keyboards, or the like, and other types of communications interfaces. Thermal printer status inputs appear on the electrical block diagram as: Printer Off Line Sensor and Printer Out of Paper.

H2O2 Dispensing System Control Processing

Figure 8:
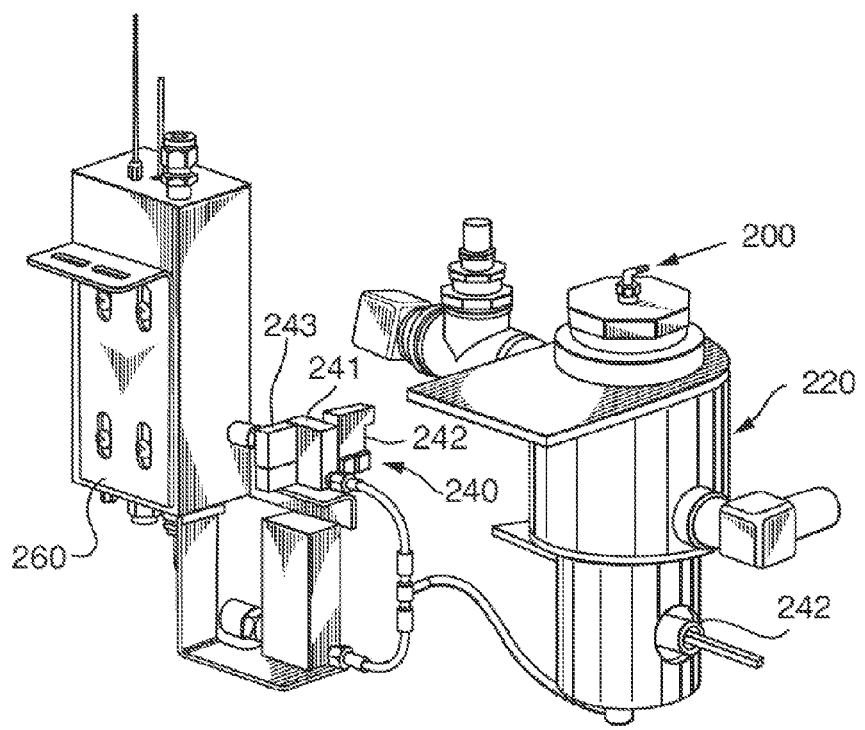
FIG. 8 shows an exemplary embodiment of a hydrogen peroxide reservoir, metering and evaporation assembly in accordance with the invention.

At the moment, two configurations of an H2O2 dispensing system are possible. The control system could be used for both systems. The first system depicted in the present application in FIG. 7 and FIG. 8 is mainly a bottle of H2O2 (180) flushed into a temperature controlled reservoir (240) FIG. 8. This first system will be described with reference to FIGS. 7,8,9 and 2. All input and output sensors described in the following appear in the list of inputs and outputs of the control system listed on FIG. 9. When the sterilizer is first initialized, the door 12 is closed and the closed position is sensed by switch S7. No bottle is sensed in the holder by (S6), the puncture needle is also retracted to the up position by the cylinder PA-01 (208). S8 and S9 provide sensing for the upward and downward position of cylinder (208). Also, actuator PA-02 is retracted in the holder unlocked position. The user is invited by the message on the screen (118) to open the door (205) and to insert a H2O2 bottle in the holder. So when the bottle is sensed by S6, another message on the screen (118) invites the user to close the door (205) which is sensed by S7. Software control is carried out by the CPU (108) and condition sensors. The bottle is set by gravity on a rotating base (209). The CPU starts the motor M-02 to rotate the bottle 180. A bar code reader BS-01 (FIG. 2,) (122) FIG. 9 reads a bar code on the bottle. The CPU verifies the expiry date of the bottle and if the bottle is past its expiry date, the door 205 remains unlocked and a message on the screen (118) invites the user to change the bottle for another one. If the date is correct, the CPU stops the motor M-02 and locks the door (205) by actuating PA-02 (FIG. 2). Then CPU actuates the cylinder (208) for the needle 209 to perforate the sealed cap of the bottle until S9 senses the needle in the down position. Then the bottle is totally emptied into the reservoir 240 by suction provided through valve (212) and vacuum from pump (40). The door (205) remains locked until all the H2O2 in the reservoir has been used. Level sensors S10 and S11 provide the conditions necessary for the CPU to estimate if another bottle is needed. If so, the needle is retracted from the bottle and the door (205) is unlocked and the user is invited by a message on the screen (118) to replace the H2O2 bottle.

Description of the Alternate and Preferred H2O2 Dispensing System

The following dispensing system does not include the cooled reservoir (240). Instead, the H2O2 remains in the bottle (180). Level detectors S10 and S11 are removed and replaced by an ultrasonic level detector which is spring loaded against a side of the bottle near the bottom and used as a low level detector to indicate to the CPU an empty bottle. Because this sensor is spring loaded, it adds too much friction on the bottle to use the motor M-02. Therefore, the user is invited by a message on the screen (118) to rotate the bottle manually until the bar code is read by (BS-01) FIG. 2 or (122) FIG. 9. If the bottle is not out of date, the user is invited to close the door (205) and the CPU locks the compartment of the bottle holder and actuates (208) to puncture down the needle. In that preferred embodiment, the H2O2 holder is temperature controlled by a Peltier cell unit. An RTD attached to the holder and connected to the temperature interface (121) sends data to the CPU (108) by Device Net network and the CPU controls by PID function the amount of power being applied to the Peltier cell unit. The Peltier unit is supplied by the 12 VDC (121) power supply used also for the air compressor driving the pneumatic system composed of SV-15, SV-16, actuators (PA-02 and PA-01) on FIG. 2. Between each cycle, the line connected between the H2O2 bottle (180) and micro valve module (240) will be purged by SV20. Near the inlet of module (240) a foam optical detector snapped on the H2O2 line will indicate the total refill of the line without air in the line.

To that point both H2O2 dispensing systems can supply the micro valves module (240). The micro valves (SV-18 and SV19) are working reciprocally for a preset duty cycle program on an on board microcontroller circuit generating the proper timing pulses for both micro-valves. That electronic circuit is activated by a signal from the CPU (108) called H2O2 pump controller signal FIG. 9. Under software control, a proper amount of H2O2 is allowed in the humidifier manifold (260, FIG. 1). This manifold is temperature controlled by the CPU (108) using data of RTD (TT-04, FIG. 1) and controlling heater HTR-01 (FIG. 1) by PID function. Then the H2O2 vaporizes in the manifold (260) and the vapor is sent to the chamber under vacuum through pipe (280, FIG. 1).

In the preceding description, for purposes of explanation, numerous details are set forth in order to provide a thorough understanding of the embodiments of the invention. However, it will be apparent to one skilled in the art that these specific details are not required in order to practice the invention. In other instances, well-known sterilizer structures and circuits are shown in block diagram or symbol form in order not to obscure the invention. For example, specific details are not provided as to whether certain parts of the sterilizer controls are implemented as a software routine, hardware circuit, firmware, or a combination thereof.

The above-described embodiments of the invention are intended to be examples only. Alterations, modifications and variations can be effected to the particular embodiments by those of skill in the art without departing from the scope of the invention, which is defined solely by the claims appended hereto.

TABLE III

| | Oxygen Circuit |
|---|---|
| FTR-01 | Oxygen Inlet Filter |
| RG-01 | Oxygen Pressure Regulator |
| SV-01 | Oxygen Supply Valve |
| PS-01 | Oxygen Pressure Switch |
| FI-01 | Oxygen Flow Indicator |
| SV-05 | Oxygen To Chamber Valve |
| | Ozone Circuit |
| | Ozone Generator |
| TT-01 | Temperature Transmitter for Ozone Generator Cooling |
| AOZ-01 | Ozone Monitor |
| | Orifice (used to regulate ozone flow to chamber) |
| SV-02 | Ozone To Chamber Valve |
| SV-04 | Ozone Dumped Valve (By-pass) |
| | Air Circuit |
| AC-01 | Air compressor |
| AT-01 | Compressed air tank |
| PS-03 | Pressure switch for air compressor |
| RG-03 | Air pressure regulator |
| PI-03 | Air Pressure indicator |
| FTR-03 | Air inlet filter |
| | Aluminium Block |
| TT-04 | Aluminium Block Temperature Transmitter |
| HTR-01 | Heating Element |
| | STERIZONE Solution Circuit |
| SV-17 | $H_2O_2$ filling valve |
| SV-21 | $H_2O_2$ vent valve |
| SV-18 | $H_2O_2$ inlet valve |
| SV-19 | $H_2O_2$ outlet valve |
| SV-20 | $H_2O_2$ purge valve |
| | STERIZONE Solution Supply System |
| S6 | Sensor (detects STERIZONE Solution container presence-absence status) |
| S7 | Sensor (detects STERIZONE Solution compartment open-close status) |
| S8 | Sensor (detects PA-01 upper position) |
| S9 | Sensor (detects PA-01 lower position) |
| S12 | Sensor (detects STERIZONE Solution compartment locked-unlocked status) |
| S13 | Sensor (detects STERIZONE Solution compartment access (fascia) opened-closed status) |
| S14 | Sensor (detects the lower level of $H_2O_2$ in the bottle) |
| S15 | Sensor (detects presence of air bubble in the line) |
| SV-15 | Air pilot valve for needle puncture actuators PM-900-014 |
| SV-16 | Air pilot valve for STERIZONE Solution compartment lock actuator |
| B-01 | Custom taper shape bottom STERIZONE Solution bottle |
| BS-01 | Barcode scanner for bottle |
| PA-01 | Pneumatic actuator for bottle puncture |
| PA-02 | Pneumatic actuator for STERIZONE Solution compartment lock |
| PA-03 | Pneumatic actuator for puncture needle centering |
| M-02 | Electric motor that rotate bottle for barcode scanning |
| CS-01 | Cooling system for the bottle |
| VS-02 | Vacuum switch (to fill and purge $H_2O_2$ line) |
| | Sterilization Chamber |
| S1 | Door Closed Upper Switch |
| S2 | Door Closed Lower Switch |
| S4 | Door Locked Switch |
| S3 | Door Unlocked Switch |
| PT-01 | Chamber Pressure Transmitter |
| VS-01 | Chamber Vacuum Switch |
| TT-03,5,6 | Chamber Temperature Transmitters |
| TT-07 | Chamber Door Temperature Transmitter |
| | Vacuum Circuit |
| SV-06 | Chamber Vacuum Valve |
| M-01 | Vacuum Pump Run status flag |
| M-01 | Vacuum Pump Contactor |
| CAT-01 | Catalytic Converter |

TABLE III-continued

| | Catalyst Drying Circuit |
|---|---|
| FTR-02 | Port muffler |
| SV-11 | Air to Catalytic Converter Valve (Catalyst Dryer Valve) PM-900-002 |
| | Cooling Circuit |
| FS-02 | Coolant Flow Switch |
| M-05 | Circulation Pump Run status flag |
| M-05 | Circulation Pump Contactor Overload Circulation Pump |
| PS-02 | Compressor Low Pressure Switch |
| M-06 | Compressor Run status flag |
| M-06 | Compressor Contactor Overload Compressor |

What is claimed is:

1. A method for sterilizing an article in a sealable sterilization chamber, comprising the steps of
a. placing the article into the sterilization chamber,
b. sealing the chamber,
c. applying to the chamber a vacuum of a first pressure, the first pressure being sufficient to evaporate an aqueous solution of hydrogen peroxide, at the temperature of an atmosphere in the chamber, to form a water vapor component and a hydrogen peroxide vapor component,
d. interrupting all removal of any component of the chamber atmosphere after applying the vacuum at least until the end of a second exposure period,
e. during a first exposure period, humidifying the chamber atmosphere solely by injecting repeated pulses of evaporated aqueous hydrogen peroxide solution, having a first hydrogen peroxide concentration, into the sealed chamber at a pulse volume of at most 75 μl, and terminating the injecting once a preselected second pressure, higher than the first pressure and in the range of 17-54 Torr, is reached in the sealed sterilization chamber to create on the article a layer of micro-condensation of hydrogen peroxide with a second hydrogen peroxide concentration higher than the first concentration;
f. during the second exposure period following the first exposure period, injecting into the chamber a dry ozone or nitric oxide containing gas, whereby the humidifying of the chamber atmosphere improves a sterilization efficiency of the dry ozone or nitric oxide containing gas to achieve sterilization of the article;
g. removing residual hydrogen peroxide, ozone, or nitric oxide containing gas from the chamber at the end of the second exposure period, and
h. removing the article from the chamber.

2. The method of claim 1, wherein the pulse volume is less than 35 μL.

3. The method of claim 2, wherein the pulse volume is about 20 μL.

4. The method of claim 1, wherein steps c) to g are repeated at least once.

5. The method of claim 1, wherein the solution is a 50% hydrogen peroxide solution and the second pressure is 20 Torr.

6. The method of claim 1, wherein an amount of ozone in the range of 1-10 mg per liter of sterilization atmosphere is injected in the injecting step f).

7. The method of claim 1, wherein the first pressure is 1 Torr (1.33 mbar).

8. The method of claim 1, wherein the second pressure is 20 Torr.

9. A method for sterilizing an article in a sealable sterilization chamber, comprising the steps of
  a. placing the article into the sterilization chamber,
  b. sealing the chamber,
  c. applying to the chamber a vacuum of a first pressure, the first pressure being sufficient to evaporate an aqueous solution of hydrogen peroxide, at the temperature of an atmosphere in the chamber, to form a water vapor component and a hydrogen peroxide vapor component, the aqueous solution having a first hydrogen peroxide concentration,
  d. interrupting all removal of any component of the chamber atmosphere after applying the vacuum at least until the end of a second exposure period,
  e. during a first exposure period, humidifying the chamber atmosphere solely by injecting into the sealed chamber repeated pulses of the evaporated aqueous hydrogen peroxide solution at a pulse volume of at most 75 μl, and terminating the injecting once a preselected second pressure, higher than the first pressure, is reached in the sealed sterilization chamber for controlling selective condensation of the hydrogen peroxide vapor component and to create a layer of micro-condensation of hydrogen peroxide on the article with a second hydrogen peroxide concentration higher than the first concentration;
  f. during the second exposure period following the first exposure period, injecting a dry ozone or nitric oxide containing gas into the chamber, whereby the humidifying of the chamber atmosphere improves a sterilization efficiency of the dry ozone or nitric oxide containing gas to achieve sterilization of the article;
  g. removing residual hydrogen peroxide, ozone, or nitric oxide containing gas from the chamber at the end of the second exposure period, and
  h. removing the article from the chamber.

10. A method for sterilizing an article in a sealable sterilization chamber, comprising the steps of
  a. placing the article into the sterilization chamber,
  b. sealing the chamber,
  c. applying to the chamber a vacuum of a first pressure, the first pressure being sufficient to evaporate an aqueous solution of hydrogen peroxide, at the temperature of an atmosphere in the chamber, to form a water vapor component and a hydrogen peroxide vapor component, the aqueous solution having a first hydrogen peroxide concentration,
  d. interrupting all removal of any component of the chamber atmosphere after applying the vacuum at least until the end of a second exposure period,
  e. during a first exposure period, humidifying the chamber atmosphere solely by injecting into the sealed chamber repeated pulses of the evaporated aqueous hydrogen peroxide solution, and terminating the injecting once a preselected second pressure, higher than the first pressure, is reached in the sealed sterilization chamber, the pulses having a volume selected for controlling selective condensation of the hydrogen peroxide vapor component to create a layer of micro-condensation of hydrogen peroxide on the article with a second hydrogen peroxide concentration higher than the first concentration and to prevent condensation at an injection site of the evaporated aqueous hydrogen peroxide solution;
  f. during the second exposure period following the first exposure period, injecting a dry ozone or nitric oxide containing gas into the chamber, whereby the humidifying of the chamber atmosphere improves a sterilization efficiency of the dry ozone or nitric oxide containing gas to achieve sterilization of the article;
  g. removing residual hydrogen peroxide, ozone, or nitric oxide containing gas from the chamber at the end of the second exposure period, and
  h. removing the article from the chamber.

* * * * *